United States Patent

Otten et al.

[11] Patent Number: 5,925,767
[45] Date of Patent: Jul. 20, 1999

[54] PYRAZOLE-4-YL-HETAROYL DERIVATIVES AS HERBICIDES

[75] Inventors: Martina Otten, Ludwigshafen; Wolfgang von Deyn, Neustadt; Stefan Engel, Idstein; Regina Luise Hill, Speyer; Uwe Kardorff; Marcus Vossen, both of Mannheim; Peter Plath, Frankenthal; Norbert Götz, Worms; Karl-Otto Westphalen, Speyer; Helmut Walter, Obrigheim; Ulf Misslitz, Neustadt, all of Germany

[73] Assignee: BASF Aktiengesellschaft, Ludwigshafen, Germany

[21] Appl. No.: 09/125,690

[22] PCT Filed: Feb. 20, 1997

[86] PCT No.: PCT/EP97/00803

§ 371 Date: Aug. 24, 1998

§ 102(e) Date: Aug. 24, 1998

[87] PCT Pub. No.: WO97/30993

PCT Pub. Date: Aug. 28, 1997

[30] Foreign Application Priority Data

Feb. 24, 1996 [DE] Germany ............... 196 07 041
Mar. 29, 1996 [DE] Germany ............... 196 12 685

[51] Int. Cl.$^6$ ..................... C07D 409/06; C07D 411/06
[52] U.S. Cl. ......................... 548/364.4; 504/282
[58] Field of Search ................ 548/364.4; 504/282

[56] References Cited

U.S. PATENT DOCUMENTS

| | | |
|---|---|---|
| 4,643,757 | 2/1987 | Baba et al. . |
| 5,506,194 | 4/1996 | Nasuno et al. . |
| 5,591,868 | 1/1997 | Nasuno et al. . |
| 5,607,898 | 3/1997 | Nakamura et al. . |

FOREIGN PATENT DOCUMENTS

| | | |
|---|---|---|
| 240 001 | 10/1987 | European Pat. Off. . |
| 282 944 | 9/1988 | European Pat. Off. . |
| 344 774 | 9/1993 | European Pat. Off. . |
| 629 623 | 12/1994 | European Pat. Off. . |
| 728 756 | 8/1996 | European Pat. Off. . |
| 94/01431 | 1/1994 | WIPO . |
| 95/04054 | 2/1995 | WIPO . |
| 95/13275 | 5/1995 | WIPO . |
| 96/25412 | 8/1996 | WIPO . |
| 96/31507 | 10/1996 | WIPO . |

OTHER PUBLICATIONS

J. F. prakt. Chem. Band 315, Heft 3, 1973, S. 382–418.

*Primary Examiner*—Robert W. Ramsuer
*Attorney, Agent, or Firm*—Keil & Weinkauf

[57] ABSTRACT

Pyrazolylhetaroyl derivatives of the formula I

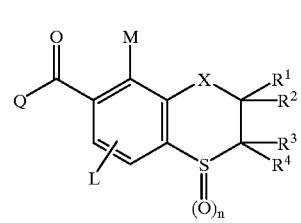

where the substituents have the following meanings:

L and M are hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen, cyano, nitro;

X is oxygen or sulfur which can be substituted by one or two oxygens;

n is zero, one or two; and

Q, $R^1$, $R^2$, $R^3$ and $R^4$ have the meanings given in claim 1, processes for the preparation of the pyrazol-4-yl-hetaroyl derivatives, compositions comprising them, and the use of these derivatives or of the compositions comprising them for controlling weeds.

11 Claims, No Drawings

PYRAZOLE-4-YL-HETAROYL DERIVATIVES AS HERBICIDES

The present invention relates to novel herbicidally active pyrazol-4-yl-hetaroyl derivatives, to processes for the preparation of the pyrazol-4-yl-hetaroyl derivatives, to compositions comprising them, and to the use of these derivatives or of the compositions comprising them for controlling weeds.

Herbicidally active pyrazolylaroyl derivatives are disclosed in the literature, for example in WO 9504054, WO 9401431 and EP 629623 and EP 344774.

However, the herbicidal properties of the known compounds and their compatibility with crop plants are only moderately satisfactory.

It is an object of the present invention to provide novel pyrazol-4-yl-hetaroyl derivatives which have improved properties.

We have found that this object is achieved by pyrazol-4-yl-hetaroyl derivatives of the formula I

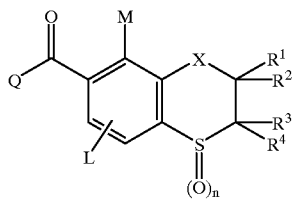

I where the substituents have the following meanings:

L and M are hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen, cyano, nitro;

X is oxygen or sulfur which can be substituted by one or two oxygens;

is zero, one, two;

$R^1$ is hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen;
  phenyl which may be mono- or polysubstituted by the following groups: $C_1$–$C_4$-alkyl, hydrogen, $C_1$–$C_4$-alkoxy, $C_1$–$C_4$-haloalkyl, $C_1$–$C_4$-haloalkoxy, halogen, nitro, cyano, $C_1$–$C_4$-alkyloxycarbonyl;

$R^2$ is hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen;
  phenyl which may be mono- or polysubstituted by the following groups: $C_1$–$C_4$-alkyl, hydrogen, $C_1$–$C_4$-alkoxy, $C_1$–$C_4$-haloalkyl, $C_1$–$C_4$-haloalkoxy, halogen, nitro, cyano, $C_1$–$C_4$-alkyloxycarbonyl; $R^2$ and $R^3$ may form a linkage;

$R^3$ is hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen;
  phenyl which may be mono- or polysubstituted by the following groups: $C_1$–$C_4$-alkyl, hydrogen, $C_1$–$C_4$-alkoxy, $C_1$–$C_4$-haloalkyl, $C_1$–$C_4$-haloalkoxy, halogen, nitro, cyano, $C_1$–$C_4$-alkyloxycarbonyl; $R^3$ and $R^2$ may form a linkage;

$R^4$ is hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen;
  phenyl which may be mono- or polysubstituted by the following groups: $C_1$–$C_4$-alkyl, hydrogen, $C_1$–$C_4$-alkoxy, $C_1$–$C_4$-haloalkyl, $C_1$–$C_4$-haloalkoxy, halogen, nitro, cyano, $C_1$–$C_4$-alkyloxycarbonyl;

Q is a pyrazole ring, linked in the 4-position, of the formula II

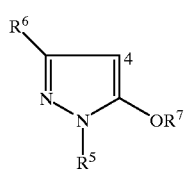

II where
  $R^5$ is $C_1$–$C_4$-alkyl,
  $R^6$ is hydrogen, $C_1$–$C_4$-alkyl or $C_1$–$C_4$-haloalkyl and
  $R^7$ is hydrogen, $C_1$–$C_4$-alkylsulfonyl, phenylsulfonyl or alkylphenylsulfonyl,
and agriculturally useful salts.

Compounds of the formula I are obtained by reacting compounds of the formula II with a benzoic acid derivative of the formula III and subjecting the product to a rearrangement reaction to give hetaroyl derivatives of the formula I.

Scheme 1

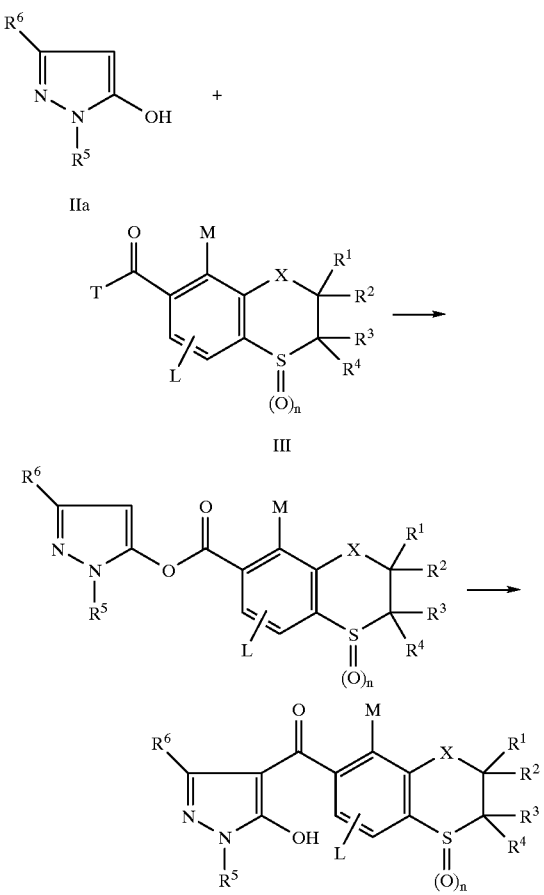

In the above Scheme 1, T in the abovementioned formulae has the meanings halogen or OH, and L, M, X, $R^1$, $R^2$, $R^3$, $R^4$, $R^5$, $R^6$ and n have the meanings given above.

The first step of the reaction sequence, the acylation, is carried out in a generally known manner, eg. by adding an acid chloride of the formula III (T=Cl) or a carboxylic acid III (T=OH) which has been activated for example with DCC (dicyclocarbodiimides [sic]) or similar agents known from the literature, eg. triphenylphosphine/DEAD=diethyl azodicarboxylate, 2-pyridine disulfide/triphenylphosphine to the solution or suspension of a cyclohexnedione II in the presence or absence of an auxiliary base. The reactants and the auxiliary base are expediently employed in equimolar amounts. A slight excess, eg. 1.2 to 1.5 mole equivalents, of the auxiliary base, based on II, may be advantageous in certain cases.

Suitable auxiliary bases are tertiary alkylamines, pyridine or alkali metal carbonates. Examples of solvents which can be used are methylene chloride, dioxane, diethyl ether, toluene, acetonitrile or ethyl acetate.

The reaction mixture is preferably cooled to 0 to 10° C. while the acid chloride is added, and the mixture is then stirred at from 20 to 100° C., in particular 25 to 50° C., until the reaction has ended. Working-up is carried out in the customary manner, for example the reaction mixture is poured into water and the product of value is extracted, for example using methylene chloride. After drying the organic phase and removing the solvent, the crude enol ester can be employed in the rearrangement reaction without further purification. Preparation Examples for benzoic esters of 5-hydroxypyrazoles are found, for example, in EP-A 282944 or in U.S. Pat. No. 4,643,757.

The rearrangement reaction of the 5-hydroxypyrazoylbenzoic [sic] esters which gives the compounds of the formula I is advantageously carried out at from 20 to 40° C. in a solvent and in the presence of an auxiliary base and, if required, with the aid of a cyano compound as catalyst.

Examples of solvents which can be used are acetonitrile, methylene chloride, tert-amyl alcohol, dioxane, 1,2-dichloroethane, ethyl acetate or toluene. Preferred solvents are acetonitrile and dioxane. Suitable auxiliary bases are tertiary alkylamines, pyridine or alkali metal carbonates, which are preferably employed in equimolar amounts or in up to 4-fold excess, based on the 5-hydroxypyrazolebenzoic [sic] ester. Preferred auxiliary bases are triethylamine and alkali metal carbonate in double amounts.

Suitable catalysts are potassium cyanide, acetone cyanohydrin and trimethylsilyl cyanide, preferably in an amount from 1 to 50 mol percent, based on the enol ester. Acetone cyanohydrin is preferably added, for example in the amount of from 5 to 15, in particular 10, mol %.

Examples of the rearrangement of benzoic esters of 5-hydroxypyrazoles are found, for example, in EP-A 282 944 or in U.S. Pat. No. 4,643,757.

Working-up is carried out in a manner known per se, for example the reaction mixture is acidified with dilute mineral acids, such as 5% strength hydrochloric acid or sulfuric acid, and extracted with an organic solvent, such as methylene chloride or ethyl acetate. To purify the extract, it is extracted using cold 5 to 10% strength alkali metal carbonate solution, the end product [lacuna] precipitated in the aqueous phase of the formula Ia–Ie or reextracted using methylene chloride or ethyl acetate, dried and subsequently freed from the solvent.

The 5-hydroxypyrazoles of the formula II which are used as starting material are known and can be prepared by processes known per se (cf. EP-A 240 001 and J. Prakt. Chem. 315 (1973), 382). 1,3-Dimethyl-5-hydroxypyrazole is a commercially available compound.

Benzoic acid derivatives of the formula III can be prepared as follows:

Benzoyl halides such as, for example, benzoyl chlorides of the formula III (T=Cl) are prepared in a manner known per se by reacting the benzoic acid of the formula III (T=OH) with thionyl chloride.

The benzoic acids of the formula III (T=OH) can be prepared in a known manner from the corresponding esters of the formula III (T=$C_1$–$C_4$-alkoxy) by acidic or alkaline hydrolysis.

The intermediates of the formula III can be synthesized starting from compounds which are known from the literature in some cases, such as substituted phenolcarboxylic acids IV or thiocarboxylic acids V. Compounds IV or V which were hitherto unknown can be synthesized by using reactions with are known from the literature (Ref.: Houben Weyl, Methoden der Organischen Chemie [Methods in Organic Chemistry] Volumes VI, IX and E11).

The further reaction which gives the intermediates of the formula III proceeds via processes known from the literature (eg. Synthesis 1975, 451; J. Org. Chem. 1974, 39–1811; J. Am. Chem. Soc. 1954, 76, 1068; Heterocyclic Compounds, Volume: Multi-Sulfur and Sulfur an Oxygen Five and Six-Membered Heterocycles; J. Org. Chem. 1979, 44, 1977).

Scheme 2

A)

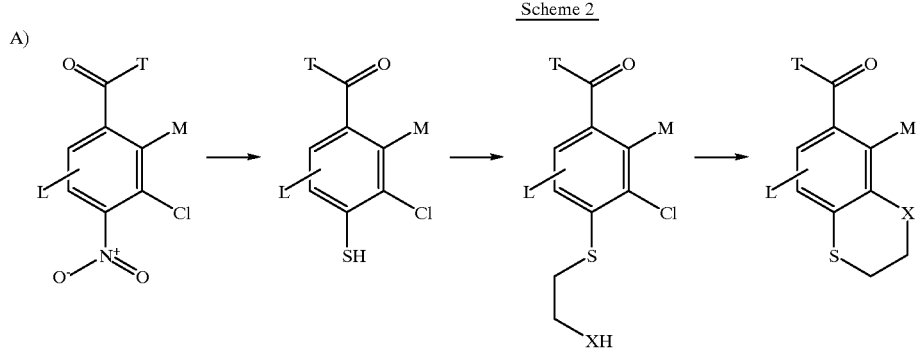

-continued
or
B)
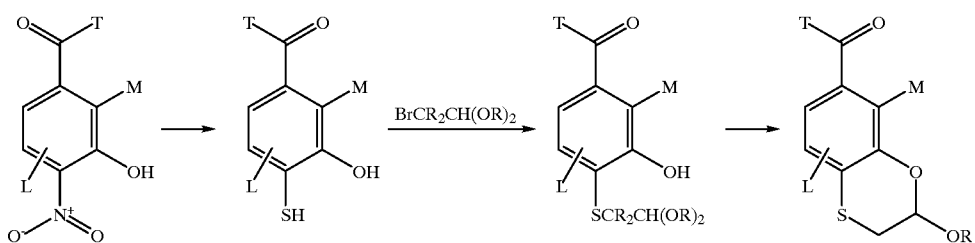
C)
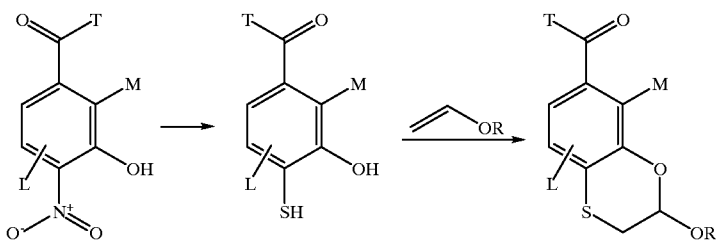
D)
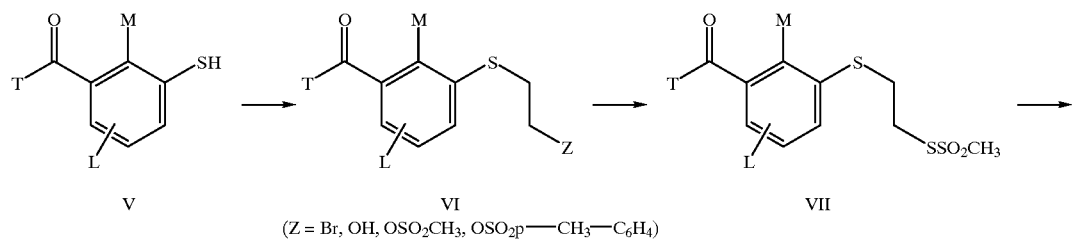
(Z = Br, OH, OSO$_2$CH$_3$, OSO$_2$p—CH$_3$—C$_6$H$_4$)
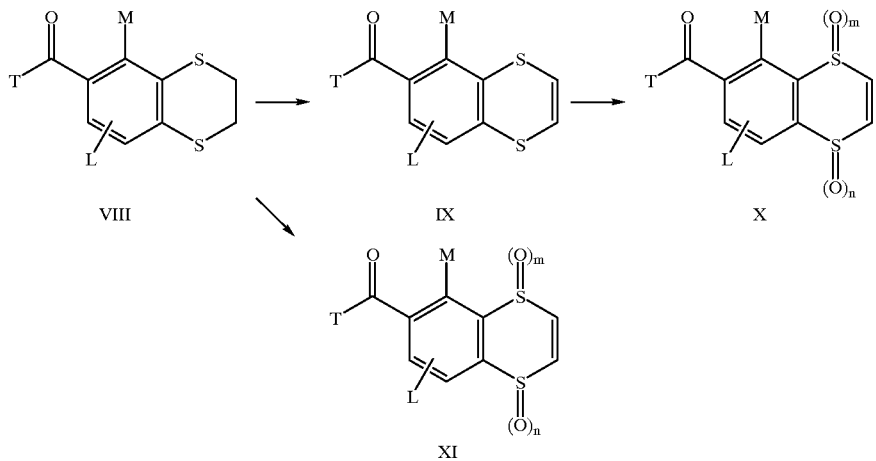

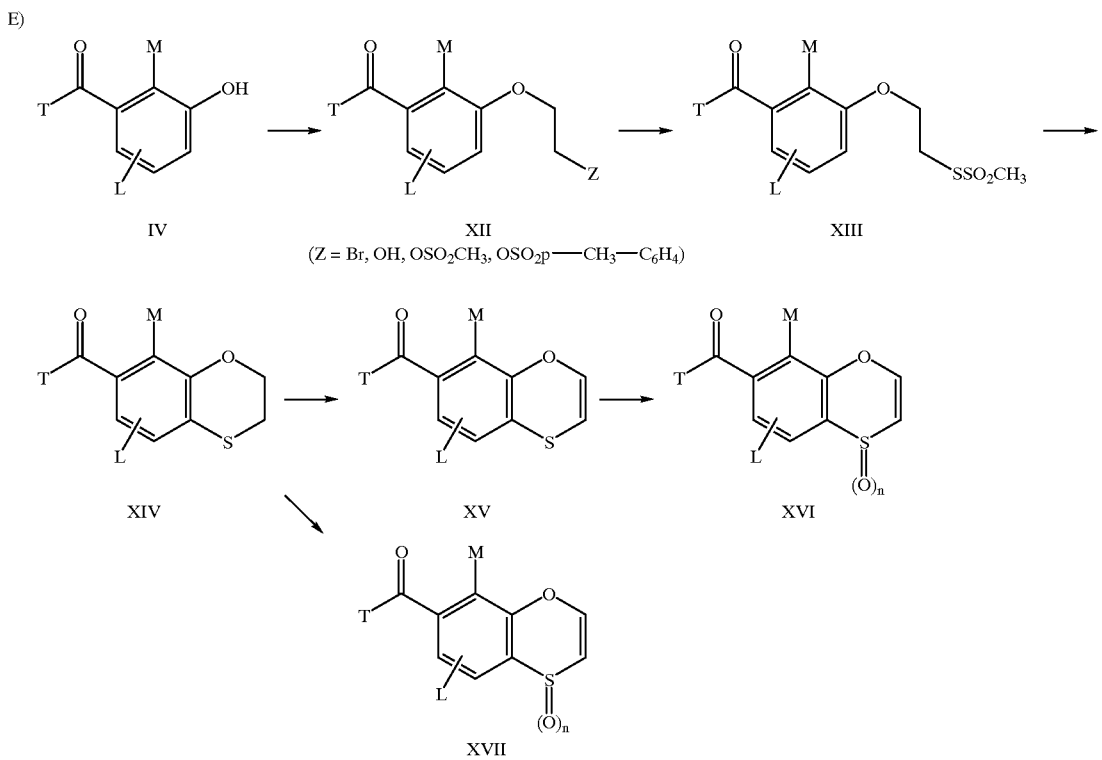

This shows that 2,3-dihydrobenz-1,4-oxathiine derivatives, eg. as outlined in Scheme 2A, can be synthesized by intramolecular nucleophili substitution on the aromatic (X=O,S; T=OH, $C_1$–$C_4$-alkoxy) (Lit.: J. Heterocycl. Chem. 20, 1983, 867) . Routes B and C describe the route to 2-alkoxy-2,3-dihydrobenz-1,4-oxathiine derivatives which is described in the literature (Lit.: J. Am. Chem. Soc. 76, 1954, 1068; J. Org. Chem. 44, 1979, 1977). As shown in Scheme 2 in D and E phenols or thiols can be alkylated with alkyl bromides in alkaline solution, for example as shown in Scheme 2 in D and E. The reactants and the base are expediently employed in equimolar amounts. An excess of base may be advantageous. Preferred sovlents are alcohols such as ethanol or DMF, and preferred bases are alcoholates, eg. sodium ethanolate or NaH. The reaction can be carried out under atmospheric or elevated pressure. The preferred pressure range is from 1 to 10 bar. The reaction mixture is preferably stirred at from 20–150° C., in particular from 60 to 80° C. Working-up is carried out for example in such a way that the reaction mixture is poured into dilute base, such as sodium hydroxide solution, and the product of value can be obtained by extraction, for example using ethyl acetate, dried and removed from the solvent.

However, this may be followed, for example, by an exchange of the Z using a solution of potassium methanethiosulfonate in alcohol. Preferred solvents are ethanol, methanol and isopropanol. The reaction mixture is preferably stirred at from 20 to 100° C., in particular at from 60 to 80° C.

Working-up is carried out for example by adding water, the product of value being filtered off with suction or extracted by extraction using, for example, methylene chloride and dried.

The cyclization reaction which gives the dihydrobenzoxathiine or dihydrobenzodithiine skeleton is carried out with the addition of a Lewis acid in an inert solvent. The preferred Lewis acid is aluminum trichloride and the preferred inert solvent is nitromethane or methylene chloride. The reaction mixture is held at from 20 to 50° C. Working-up is carried out for example by adding dilute mineral acid, such as hydrochloric acid, and the product of value is filtered off with suction or extracted by extraction with ether, dried and freed from the solvent.

The compounds can be functionalized further by means of oxidation by processes known from the literature and/or dehydrogenation (Houben Weyl Methoden der Organischen Synthese [Methods in Organic Synthesis] Volume IV/1a and b).

Alternatively, the benzoic acids of the formula III can be obtained by reacting the corresponding bromine- or iodine-substituted compounds of the formula XVIII Scheme 3

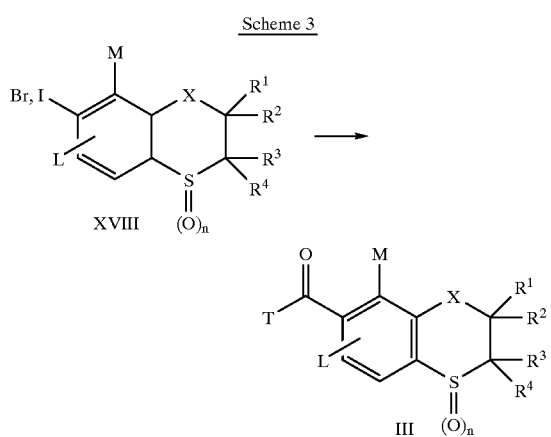

where

T is OH, $C_1$–$C_4$-alkoxy; and

L, M, X, $R^1$ to $R^4$ and n have the above-described meanings with carbon monoxide and water in the presence of a palladium, nickel, cobalt or rhodium transition metal catalyst and a base.

The catalysts nickel, cobalt, rhodium and, in particular, palladium can exist as metals or in the form of customary salts, such as in the form of halogen compounds, eg. $PdCl_2$, $RhCl_3·H_2O$, acetates, eg. $Pd(OAc)_2$, cyanides and the like, in the known valency stages. Furthermore, metal complexes with tertiary phosphines, metal alkylcarbonyls, metal carbonyls, eg. $CO_2(CO)_8$, $Ni(CO)_4$, metal carbonyl complexes with tertiary phosphines, eg. $(PPh_3)_2Ni(CO)_2$, or transition metal salts complexed with tertiary phosphines may be present. The last-mentioned embodiment is particularly preferred when palladium is used as the catalyst. The nature of the phosphine ligands can be varied within a broad range. For example, they can be represented by the following formulae:

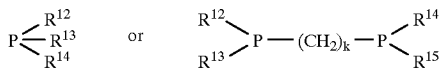

where k is the number 1, 2, 3 or 4 and the radicals $R^{12}$ to $R^{15}$ are low-molecular-weight alkyl, eg. $C_1$–$C_6$-alkyl, aryl, $C_1$–$C_4$-alkylaryl, eg. benzyl, phenethyl or aryloxy. Aryl is, for example, naphthyl, anthryl and, preferably, unsubstituted or substituted phenyl, where the substituents can be varied within a broad range provided that they are inert with regard to the carboxylation reaction, and embrace all inert C-organic radicals, such as $C_1$–$C_6$-alkyl radicals, eg. methyl, carboxyl radicals such as COOH, COOM (M is, for example, an alkali metal salt, alkaline earth metal salt or ammonium salt), or C-organic radicals which are linked via oxygen, such as $C_1$–$C_6$-alkoxy radicals.

The phosphine complexes can be prepared in a manner known per se, for example as described in the documents mentioned at the outset. For example, customary commercially available metal salts, such as $PdCl_2$ or $Pd(OCOCH_3)_2$, are used as the starting material, and the phosphine, eg. $P(C_6H_5)_3$, $P(n-C_4H_9)_3$, $PCH_3(C_6H_5)_2$, 1,2-bis (diphenylphosphino)ethane is added.

The amount of phosphine, based on the transition metal, is normally 0 to 20, in particular 0.1 to 10, mole equivalents, especially preferably 1 to 5 mole equivalents.

The amount of transition metal is not critical. For cost reasons, one will, of course, rather use a small amount, eg. from 0.1 to 10 mol %, in particular 1 to 5 mol %, based on the starting material II or III.

To prepare the benzoic acids III (T=OH) the reaction is carried out with carbon monoxide and at least equimolar amounts of water, based on the starting materials VI. The reactant water can simultaneously also act as the solvent, ie. the maximum amount is not critical.

However, depending on the nature of the starting materials and the catalysts used, it may also be advantageous to use, instead of the reactant, another inert solvent or the base used for the carboxylation as the solvent.

Suitable inert solvents are solvents which are customary for carboxylation reactions, such as hydrocarbons, eg. toluene, xylene, hexane, pentane, cyclohexane, ethers, eg. methyl tert-butyl ether, tetrahydrofuran, dioxane, dimethoxy ethane, substituted amides such as dimethylformamide, persubstituted ureas such as tetra-$C_1$–$C_4$-alkylureas or nitriles such as benzonitrile or acetonitrile.

In a preferred embodiment of the process, one of the reactants, in particular the base, is used in an excess, thus dispensing with an additional solvent.

Bases which are suitable for the process are all inert bases which are capable of binding the hydrogen iodide, or hydrogen bromide, which is liberated during the reaction. Examples are tertiary amines such as tert-alkylamines, eg. trialkylamines such as triethylamine, cyclic amines such as N-methylpiperidine or N,N'-dimethylpiperazine, pyridine, alkali metal [lacuna] or hydrogen carbonates, or tetraalkyl-substituted urea derivatives such as tetra-$C_1$–$C_4$-alkylurea, eg. tetramethylurea.

The amount of base is not critical, 1 to 10, in particular 1 to 5, mol are normally used. When simultaneously using the base as the solvent, the amount is generally selected in such a way that the reactants are dissolved, but unnecessarily high excesses are avoided for practical reasons, to save costs, to be able to use small reaction vessels and to guarantee maximum contact between the reactants.

During the reaction, the carbon monoxide pressure is adjusted in such a way that there is always an excess of CO, based on VI. The carbon monoxide pressure at room temperature is preferably from 1 to 250 bar, in particular from 5 to 150 bar, Co.

The carbonylation is generally carried out at from 20 to 250° C., in particular from 30 to 150° C., either continuously or batchwise. In the case of batchwise operation, it is expedient to inject carbon monoxide continuously onto the reaction mixture to maintain a constant pressure.

Those arylhalogen compounds XVIII used as starting compounds which have not already been disclosed can be prepared readily by a suitable combination of known syntheses and by the above-described reaction sequences.

With a view to the intended use of the pyrazoylhetaroyl [sic] derivatives of the general formula I, the following radicals are suitable as substituents.

L and M hydrogen, $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 1,1,2-trimethylpropyl, 1,2,2-trimethylpropyl, 1-ethyl-1-methylpropyl or 1-ethyl-2-methyl-propyl, in particular methyl, ethyl, 1-methylethyl, 1-methylpropyl, 2-methylpropyl, 1,1-dimethylethyl and 1,1-dimethylpropyl;

$C_2$–$C_6$-alkenyl such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-4-butenyl, 3-methyl-3 butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3 pentenyl [sic], 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3 butenyl [sic], 2-ethyl-2-butenyl, 2-ethyl-3-butenyl, 1,1,2-trimethyl-2-propenyl, 1-ethyl-1-methyl-2-propenyl and ethyl-2-methyl-2-propenyl, in particular 1-methyl-2-propenyl, 1-methyl-2-butenyl, 1,1-dimethyl-2-propenyl and 1,1-dimethyl-2-butenyl;

$C_2-C_6$-alkynyl, such as propargyl, 2-butynyl, 3-butynyl, 2-pentynyl, 3-pentynyl, 4-pentynyl, 1-methyl-3-butynyl, 2-methyl-3-butynyl, 1-methyl-2-butynyl, 1,1-dimethyl-2 propynyl [sic], 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

$C_1-C_4$-alkoxy, such as methoxy, ethoxy, n-propoxy, 1-methylethoxy, n-butoxy, 1-methylpropoxy, 2-methylpropoxy and 1,1-dimethylethoxy, in particular $C_1-C_3$-alkoxy, such as methoxy, ethoxy and i-propoxy, it being possible for these groups to be unsubstituted or substituted by one to five halogen atoms, such as fluorine, chlorine, bromine and iodine, preferably fluorine and chlorine, or $C_1-C_4$-alkoxy as mentioned above.

Preferred pyrazol-4-yl-hetaroyl derivatives are those of the formula Ia

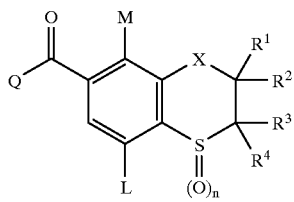

Ia where L is hydrogen, $C_1-C_6$-alkyl, $C_2-C6$-alkenyl, $C_2-C_6$-alkynyl, $C_1-C_4$-alkoxy, $C_1-C_4$-haloalkyl, $C_1-C_4$-haloalkoxy, halogen, cyano or nitro and M is hydrogen, $C_1-C_6$-alkyl, $C_2-C_6$-alkenyl, $C_2-C_6$-alkynyl, $C_1-C_4$-alkoxy, $C_1-C_4$-haloalkyl, $C_1-C_4$-haloalkoxy, halogen, cyano or nitro and Q, X, $R_1$ to $R_4$ and n have the abovementioned meanings.

Further preferred pyrazol-4-yl-hetaroyl derivatives are those of the formula Ib

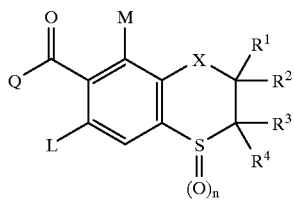

Ib where L is $C_1-C_6$-alkyl, $C_2-C_6$-alkenyl, $C_2-C_6$-alkynyl, $C_1-C_4$-alkoxy, $C_1-C_4$-halo-alkyl, $C_1-C_4$-haloalkoxy, halogen, cyano or nitro and M is hydrogen, $C_1-C_6$-alkyl, $C_2-C_6$-alkenyl, $C_2-C_6$-alkynyl, $C_1-C_4$-alkoxy, $C_1-C_4$-haloalkyl, $C_1-C_4$-haloalkoxy, halogen, cyano or nitro and Q, X, $R_1$ to $R_4$ and n have the abovementioned meanings.

Other preferred pyrazol-4-yl-hetaroyl derivatives of the formula I are those where the radicals L and M are hydrogen, methyl, methoxy, chlorine, cyano, nitro and trifluoromethyl.

Further preferred pyrazol-4-yl-hetaroyl derivatives are also those of the formula Ic

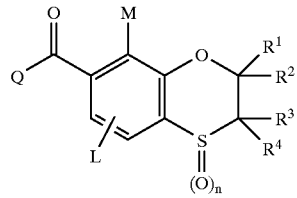

Ic where L is hydrogen, $C_1-C_6$-alkyl, $C_2-C_6$-alkenyl, $C_2-C_6$-alkynyl, $C_1-C_4$-alkoxy, $C_1-C_4$-haloalkyl, $C_1-C_4$-haloalkoxy, halogen, cyano or nitro and M is hydrogen, $C_1-C_6$-alkyl, $C_2-C_6$-alkenyl, $C_2-C_6$-alkynyl, $C_1-C_4$-alkoxy, $C_1-C_4$-haloalkyl, $C_1-C_4$-haloalkoxy, halogen, cyano or nitro and Q, $R_1$ to $R_4$ and n have the abovementioned meanings.

Other preferred pyrazol-4-yl-hetaroyl derivatives are those of the formula Id

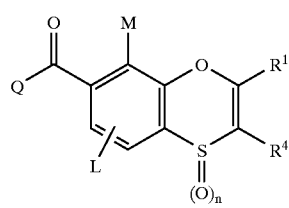

Id where L is hydrogen, $C_1-C_6$-alkyl, $C_2-C_6$-alkenyl, $C_2-C_6$-alkynyl, $C_1-C_4$-alkoxy, $C_1-C_4$-haloalkyl, $C_1-C_4$-haloalkoxy, halogen, cyano or nitro and Q, $R_1$, $R_4$ and n have the abovementioned meanings.

Further preferred pyrazol-4-yl-hetaroyl derivatives are those of the formula Id [sic]

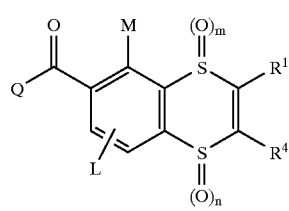

Id[sic]

where L is hydrogen, $C_1-C_6$-alkyl, $C_2-C_6$-alkenyl, $C_2-C_6$-alkynyl, $C_1-C_4$-alkoxy, $C_1-C_4$-haloalkyl, $C_1-C_4$-haloalkoxy, halogen, cyano or nitro and M is hydrogen, $C_1-C_6$-alkyl, $C_2-C_6$-alkenyl, $C_2-C_6$-alkynyl, $C_1-C_4$-alkoxy, $C_1-C_4$-haloalkyl, $C_1-C_4$-haloalkoxy, halogen, cyano or nitro and m is zero, one or two and Q, $R_1$, $R_4$ and n have the abovementioned meanings.

Also preferred pyrazol-4-yl-hetaroyl derivatives are those of the formula Ie

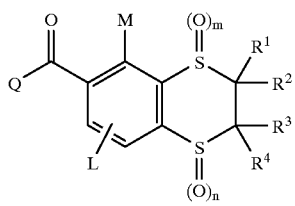

Ie[sic]

where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and m is zero, one or two and Q, $R_1$ to $R_4$ and n have the abovementioned meanings.

Other preferred pyrazol-4-yl-hetaroyl derivatives are those of the formula I to Id whose substituents consist of a combination of the preferred substituents.

Especially preferred compounds of the formula I are listed in Tables 1–2 below.

TABLE 1

Compound of the structure

| No. | $R^5$ | $R^6$ | $R^7$ | n | $R^1$ | $R^2$ | $R^3$ | $R^4$ | X | L | M |
|---|---|---|---|---|---|---|---|---|---|---|---|
| 1.1 | $CH_3$ | $CH_3$ | H | 0 | H | H | H | H | O | H | H |
| 1.2 | $CH_3$ | $CH_3$ | H | 2 | H | H | H | H | O | H | H |
| 1.3 | $CH_3$ | $CH_3$ | R | 0 | H | H | H | H | S | H | H |
| 1.4 | $CH_3$ | $CH_3$ | H | 2 | H | H | H | H | S | H | H |
| 1.5 | $CH_3$ | $CH_3$ | H | 0 | H | H | H | H | $SO_2$ | H | H |
| 1.6 | $CH_3$ | $CH_3$ | H | 2 | H | H | H | H | $SO_2$ | H | H |
| 1.7 | $CH_3$ | $CH_3$ | H | 0 | $CH_3$ | H | H | H | O | H | H |
| 1.8 | $CH_3$ | $CH_3$ | H | 2 | $CH_3$ | H | H | H | O | H | H |
| 1.9 | $CH_3$ | $CH_3$ | H | 0 | $CH_3$ | H | H | H | S | H | H |
| 1.10 | $CH_3$ | $CH_3$ | H | 2 | $CH_3$ | H | H | H | S | H | H |
| 1.11 | $CH_3$ | $CH_3$ | H | 0 | $CH_3$ | H | H | H | $SO_2$ | H | H |
| 1.12 | $CH_3$ | $CH_3$ | H | 2 | $CH_3$ | H | H | H | $SO_2$ | H | H |
| 1.13 | $CH_3$ | $CH_3$ | H | 0 | $CH_3$ | H | $CH_3$ | H | O | H | H |
| 1.14 | $CH_3$ | $CH_3$ | H | 2 | $CH_3$ | H | $CH_3$ | H | O | H | H |
| 1.15 | $CH_3$ | $CH_3$ | H | 0 | $CH_3$ | H | $CH_3$ | H | S | H | H |
| 1.16 | $CH_3$ | $CH_3$ | H | 2 | $CH_3$ | H | $CH_3$ | H | S | H | H |
| 1.17 | $CH_3$ | $CH_3$ | H | 0 | $CH_3$ | H | $CH_3$ | H | $SO_2$ | H | H |
| 1.18 | $CH_3$ | $CH_3$ | H | 2 | $CH_3$ | H | $CH_3$ | H | $SO_2$ | H | H |
| 1.19 | $CH_3$ | $CH_3$ | H | 0 | $CH_3$ | $CH_3$ | H | H | O | H | H |
| 1.20 | $CH_3$ | $CH_3$ | H | 2 | $CH_3$ | $CH_3$ | H | H | O | H | H |
| 1.21 | $CH_3$ | $CH_3$ | H | 0 | H | H | $CH_3$ | $CH_3$ | O | H | H |
| 1.22 | $CH_3$ | $CH_3$ | H | 2 | H | H | $CH_3$ | $CH_3$ | O | H | H |
| 1.23 | $C_2H_5$ | H | H | 0 | H | H | H | H | O | H | H |
| 1.24 | $C_2H_5$ | H | H | 2 | H | H | H | H | O | H | H |
| 1.25 | $C_2H_5$ | H | H | 0 | H | H | H | H | S | H | H |
| 1.26 | $C_2H_5$ | H | H | 2 | H | H | H | H | S | H | H |
| 1.27 | $C_2H_5$ | H | H | 0 | H | H | H | H | $SO_2$ | H | H |
| 1.28 | $C_2H_5$ | H | H | 2 | H | H | H | H | $SO_2$ | H | H |
| 1.29 | $C_2H_5$ | H | H | 0 | $CH_3$ | H | H | H | O | H | H |
| 1.30 | $C_2H_5$ | H | H | 2 | $CH_3$ | H | H | H | O | H | H |
| 1.31 | $C_2H_5$ | H | H | 0 | $CH_3$ | H | H | H | S | H | H |
| 1.32 | $C_2H_5$ | H | H | 2 | $CH_3$ | H | H | H | S | H | H |
| 1.33 | $C_2H_5$ | H | H | 0 | $CH_3$ | H | H | H | $SO_2$ | H | H |
| 1.34 | $C_2H_5$ | H | H | 2 | $CH_3$ | H | H | H | $SO_2$ | H | H |
| 1.35 | $C_2H_5$ | H | H | 0 | $CH_3$ | H | $CH_3$ | H | O | H | H |
| 1.36 | $C_2H_5$ | H | H | 2 | $CH_3$ | H | $CH_3$ | H | O | H | H |
| 1.37 | $C_2H_5$ | H | H | 0 | $CH_3$ | H | $CH_3$ | H | S | H | H |
| 1.38 | $C_2H_5$ | H | H | 2 | $CH_3$ | H | $CH_3$ | H | S | H | H |
| 1.39 | $C_2H_5$ | H | H | 0 | $CH_3$ | H | $CH_3$ | H | $SO_2$ | H | H |
| 1.40 | $C_2H_5$ | H | H | 2 | $CH_3$ | H | $CH_3$ | H | $SO_2$ | H | H |
| 1.41 | $C_2H_5$ | H | H | 0 | $CH_3$ | $CH_3$ | H | H | O | H | H |
| 1.42 | $C_2H_5$ | H | H | 2 | $CH_3$ | $CH_3$ | H | H | O | H | H |
| 1.43 | $C_2H_5$ | H | H | 0 | H | H | $CH_3$ | $CH_3$ | O | H | H |
| 1.44 | $C_2H_5$ | H | H | 2 | H | H | $CH_3$ | $CH_3$ | O | H | H |
| 1.45 | $CH_3$ | H | H | 0 | H | H | H | H | O | H | $CH_3$ |
| 1.46 | $CH_3$ | H | H | 2 | H | H | H | H | O | H | $CH_3$ |
| 1.47 | $CH_3$ | H | H | 0 | H | H | H | H | S | H | $CH_3$ |
| 1.48 | $CH_3$ | H | H | 2 | H | H | H | H | S | H | $CH_3$ |

TABLE 1-continued

Compound of the structure

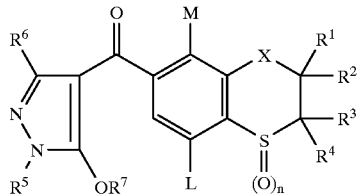

| No. | R⁵ | R⁶ | R⁷ | n | R¹ | R² | R³ | R⁴ | X | L | M |
|---|---|---|---|---|---|---|---|---|---|---|---|
| 1.49 | CH₃ | H | H | 0 | H | H | H | H | SO₂ | H | CH₃ |
| 1.50 | CH₃ | H | H | 2 | H | H | H | H | SO₂ | H | CH₃ |
| 1.51 | CH₃ | H | H | 0 | CH₃ | H | H | H | O | H | CH₃ |
| 1.52 | CH₃ | H | H | 2 | CH₃ | H | H | H | O | H | CH₃ |
| 1.53 | CH₃ | H | H | 0 | CH₃ | H | H | H | S | H | CH₃ |
| 1.54 | CH₃ | H | H | 2 | CH₃ | H | H | H | S | H | CH₃ |
| 1.55 | CH₃ | H | H | 0 | CH₃ | H | H | H | SO₂ | H | CH₃ |
| 1.56 | CH₃ | H | H | 2 | CH₃ | H | H | H | SO₂ | H | CH₃ |
| 1.57 | CH₃ | H | H | 0 | CH₃ | H | CH₃ | H | O | H | CH₃ |
| 1.58 | CH₃ | H | H | 2 | CH₃ | H | CH₃ | H | O | H | CH₃ |
| 1.59 | CH₃ | H | H | 0 | CH₃ | H | CH₃ | H | S | H | CH₃ |
| 1.60 | CH₃ | H | H | 2 | CH₃ | H | CH₃ | H | S | H | CH₃ |
| 1.61 | CH₃ | H | H | 0 | CH₃ | H | CH₃ | H | SO₂ | H | CH₃ |
| 1.62 | CH₃ | H | H | 2 | CH₃ | H | CH₃ | H | SO₂ | H | CH₃ |
| 1.63 | CH₃ | H | H | 0 | CH₃ | CH₃ | H | H | O | H | CH₃ |
| 1.64 | CH₃ | H | H | 2 | CH₃ | CH₃ | H | H | O | H | CH₃ |
| 1.65 | CH₃ | H | H | 0 | H | H | CH₃ | CH₃ | O | H | CH₃ |
| 1.66 | CH₃ | H | H | 2 | H | H | CH₃ | CH₃ | O | H | CH₃ |
| 1.67 | C₂H₅ | H | H | 0 | H | H | H | H | O | H | CH₃ |
| 1.68 | C₂H₅ | H | H | 2 | H | H | H | H | O | H | CH₃ |
| 1.69 | C₂H₅ | H | H | 0 | H | H | H | H | S | H | CH₃ |
| 1.70 | C₂H₅ | H | H | 2 | H | H | H | H | S | H | CH₃ |
| 1.71 | C₂H₅ | H | H | 0 | H | H | H | H | SO₂ | H | CH₃ |
| 1.72 | C₂H₅ | H | H | 2 | H | H | H | H | SO₂ | H | CH₃ |
| 1.73 | C₂H₅ | H | H | 0 | CH₃ | H | H | H | O | H | CH₃ |
| 1.74 | C₂H₅ | H | H | 2 | CH₃ | H | H | H | O | H | CH₃ |
| 1.75 | C₂H₅ | H | H | 0 | CH₃ | H | H | H | S | H | CH₃ |
| 1.76 | C₂H₅ | H | H | 2 | CH₃ | H | H | H | S | H | CH₃ |
| 1.77 | C₂H₅ | H | H | 0 | CH₃ | H | H | H | SO₂ | H | CH₃ |
| 1.78 | C₂H₅ | H | H | 2 | CH₃ | H | H | H | SO₂ | H | CH₃ |
| 1.79 | C₂H₅ | H | H | 0 | CH₃ | H | CH₃ | H | O | H | CH₃ |
| 1.80 | C₂H₅ | H | H | 2 | CH₃ | H | CH₃ | H | O | H | CH₃ |
| 1.81 | C₂H₅ | H | H | 0 | CH₃ | H | CH₃ | H | S | H | CH₃ |
| 1.82 | C₂H₅ | H | H | 2 | CH₃ | H | CH₃ | H | S | H | CH₃ |
| 1.83 | C₂H₅ | H | H | 0 | CH₃ | H | CH₃ | H | SO₂ | H | CH₃ |
| 1.84 | C₂H₅ | H | H | 2 | CH₃ | H | CH₃ | H | SO₂ | H | CH₃ |
| 1.85 | C₂H₅ | H | H | 0 | CH₃ | CH₃ | H | H | O | H | CH₃ |
| 1.86 | C₂H₅ | H | H | 2 | CH₃ | CH₃ | H | H | O | H | CH₃ |
| 1.87 | C₂H₅ | H | H | 0 | H | H | CH₃ | CH₃ | O | H | CH₃ |
| 1.88 | C₂H₅ | H | H | 2 | H | H | CH₃ | CH₃ | O | H | CH₃ |
| 1.89 | CH₃ | H | H | 0 | H | H | H | H | O | H | Cl |
| 1.90 | CH₃ | H | H | 2 | H | H | H | H | O | H | Cl |
| 1.91 | CH₃ | H | H | 0 | H | H | H | H | S | H | Cl |
| 1.92 | CH₃ | H | H | 2 | H | H | H | H | S | H | Cl |
| 1.93 | CH₃ | H | H | 0 | H | H | H | H | SO₂ | H | Cl |
| 1.94 | CH₃ | H | H | 2 | H | H | H | H | SO₂ | H | Cl |
| 1.95 | CH₃ | H | H | 0 | CH₃ | H | H | H | O | H | Cl |
| 1.96 | CH₃ | H | H | 2 | CH₃ | H | H | H | O | H | Cl |
| 1.97 | CH₃ | H | H | 0 | CH₃ | H | H | H | S | H | Cl |
| 1.98 | CH₃ | H | H | 2 | CH₃ | H | H | H | S | H | Cl |
| 1.99 | CH₃ | H | H | 0 | CH₃ | H | H | H | SO₂ | H | Cl |
| 1.100 | CH₃ | H | H | 2 | CH₃ | H | H | H | SO₂ | H | Cl |
| 1.101 | CH₃ | H | H | 0 | CH₃ | H | CH₃ | H | O | H | Cl |
| 1.102 | CH₃ | H | H | 2 | CH₃ | H | CH₃ | H | O | H | Cl |
| 1.103 | CH₃ | H | H | 0 | CH₃ | H | CH₃ | H | S | H | Cl |
| 1.104 | CH₃ | H | H | 2 | CH₃ | H | CH₃ | H | S | H | Cl |
| 1.105 | CH₃ | H | H | 0 | CH₃ | H | CH₃ | H | SO₂ | H | Cl |
| 1.106 | CH₃ | H | H | 2 | CH₃ | H | CH₃ | H | SO₂ | H | Cl |
| 1.107 | CH₃ | H | H | 0 | CH₃ | CH₃ | H | H | O | H | Cl |
| 1.108 | CH₃ | H | H | 2 | CH₃ | CH₃ | H | H | O | H | Cl |
| 1.109 | CH₃ | H | H | 0 | H | H | CH₃ | CH₃ | O | H | Cl |
| 1.110 | CH₃ | H | H | 2 | H | H | CH₃ | CH₃ | O | H | Cl |
| 1.111 | C₂H₅ | H | H | 0 | H | H | H | H | O | H | Cl |
| 1.112 | C₂H₅ | H | H | 2 | H | H | H | H | O | H | Cl |

TABLE 1-continued

Compound of the structure

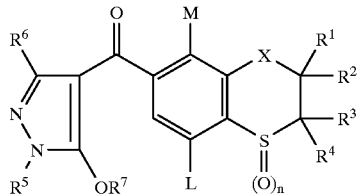

| No. | R⁵ | R⁶ | R⁷ | n | R¹ | R² | R³ | R⁴ | X | L | M |
|---|---|---|---|---|---|---|---|---|---|---|---|
| 1.113 | C₂H₅ | H | H | 0 | H | H | H | H | S | H | Cl |
| 1.114 | C₂H₅ | H | H | 2 | H | H | H | H | S | H | Cl |
| 1.115 | C₂H₅ | H | H | 0 | H | H | H | H | SO₂ | H | Cl |
| 1.116 | C₂H₅ | H | H | 2 | H | H | H | H | SO₂ | H | Cl |
| 1.117 | C₂H₅ | H | H | 0 | CH₃ | H | H | H | O | H | Cl |
| 1.118 | C₂H₅ | H | H | 2 | CH₃ | H | H | H | O | H | Cl |
| 1.119 | C₂H₅ | H | H | 0 | CH₃ | H | H | H | S | H | Cl |
| 1.120 | C₂H₅ | H | H | 2 | CH₃ | H | H | H | S | H | Cl |
| 1.121 | C₂H₅ | H | H | 0 | CH₃ | H | H | H | SO₂ | H | Cl |
| 1.122 | C₂H₅ | H | H | 2 | CH₃ | H | H | H | SO₂ | H | Cl |
| 1.123 | C₂H₅ | H | H | 0 | CH₃ | H | CH₃ | H | O | H | Cl |
| 1.124 | C₂H₅ | H | H | 2 | CH₃ | H | CH₃ | H | O | H | Cl |
| 1.125 | C₂H₅ | H | H | 0 | CH₃ | H | CH₃ | H | S | H | Cl |
| 1.126 | C₂H₅ | H | H | 2 | CH₃ | H | CH₃ | H | S | H | Cl |
| 1.127 | C₂H₅ | H | H | 0 | CH₃ | H | CH₃ | H | SO₂ | H | Cl |
| 1.128 | C₂H₅ | H | H | 2 | CH₃ | H | CH₃ | H | SO₂ | H | Cl |
| 1.129 | C₂H₅ | H | H | 0 | CH₃ | CH₃ | H | H | O | H | Cl |
| 1.130 | C₂H₅ | H | H | 2 | CH₃ | CH₃ | H | H | O | H | Cl |
| 1.131 | C₂H₅ | H | H | 0 | H | H | CH₃ | CH₃ | O | H | Cl |
| 1.132 | C₂H₅ | H | H | 2 | H | H | CH₃ | CH₃ | O | H | Cl |
| 1.133 | CH₃ | H | H | 0 | H | H | H | H | O | Cl | Cl |
| 1.134 | CH₃ | H | H | 2 | H | H | H | H | O | Cl | Cl |
| 1.135 | CH₃ | H | H | 0 | H | H | H | H | S | Cl | Cl |
| 1.136 | CH₃ | H | H | 2 | H | H | H | H | S | Cl | Cl |
| 1.137 | CH₃ | H | H | 0 | H | H | H | H | SO₂ | Cl | Cl |
| 1.138 | CH₃ | H | H | 2 | H | H | H | H | SO₂ | Cl | Cl |
| 1.139 | CH₃ | H | H | 0 | CH₃ | H | H | H | O | Cl | Cl |
| 1.140 | CH₃ | H | H | 2 | CH₃ | H | H | H | O | Cl | Cl |
| 1.141 | CH₃ | H | H | 0 | CH₃ | H | H | H | S | Cl | Cl |
| 1.142 | CH₃ | H | H | 2 | CH₃ | H | H | H | S | Cl | Cl |
| 1.143 | CH₃ | H | H | 0 | CH₃ | H | H | H | SO₂ | Cl | Cl |
| 1.144 | CH₃ | H | H | 2 | CH₃ | H | H | H | SO₂ | Cl | Cl |
| 1.145 | CH₃ | H | H | 0 | CH₃ | H | CH₃ | H | O | Cl | Cl |
| 1.146 | CH₃ | H | H | 2 | CH₃ | H | CH₃ | H | O | Cl | Cl |
| 1.147 | CH₃ | H | H | 0 | CH₃ | H | CH₃ | H | S | Cl | Cl |
| 1.148 | CH₃ | H | H | 2 | CH₃ | H | CH₃ | H | S | Cl | Cl |
| 1.149 | CH₃ | H | H | 0 | CH₃ | H | CH₃ | H | SO₂ | Cl | Cl |
| 1.150 | CH₃ | H | H | 2 | CH₃ | H | CH₃ | H | SO₂ | Cl | Cl |
| 1.151 | CH₃ | H | H | 0 | CH₃ | CH₃ | H | H | O | Cl | Cl |
| 1.152 | CH₃ | H | H | 2 | CH₃ | CH₃ | H | H | O | Cl | Cl |
| 1.153 | CH₃ | H | H | 0 | H | H | CH₃ | CH₃ | O | Cl | Cl |
| 1.154 | CH₃ | H | H | 2 | H | H | CH₃ | CH₃ | O | Cl | Cl |
| 1.155 | C₂H₅ | H | H | 0 | H | H | H | H | O | Cl | Cl |
| 1.156 | C₂H₅ | H | H | 2 | H | H | H | H | O | Cl | Cl |
| 1.157 | C₂H₅ | H | H | 0 | H | H | H | H | S | Cl | Cl |
| 1.158 | C₂H₅ | H | H | 2 | H | H | H | H | S | Cl | Cl |
| 1.159 | C₂H₅ | H | H | 0 | H | H | H | H | SO₂ | Cl | Cl |
| 1.160 | C₂H₅ | H | H | 2 | H | H | H | H | SO₂ | Cl | Cl |
| 1.161 | C₂H₅ | H | H | 0 | CH₃ | H | H | H | O | Cl | Cl |
| 1.162 | C₂H₅ | H | H | 2 | CH₃ | H | H | H | O | Cl | Cl |
| 1.163 | C₂H₅ | H | H | 0 | CH₃ | H | H | H | S | Cl | Cl |
| 1.164 | C₂H₅ | H | H | 2 | CH₃ | H | H | H | S | Cl | Cl |
| 1.165 | C₂H₅ | H | H | 0 | CH₃ | H | H | H | SO₂ | Cl | Cl |
| 1.166 | C₂H₅ | H | H | 2 | CH₃ | H | H | H | SO₂ | Cl | Cl |
| 1.167 | C₂H₅ | H | H | 0 | CH₃ | H | CH₃ | H | O | Cl | Cl |
| 1.168 | C₂H₅ | H | H | 2 | CH₃ | H | CH₃ | H | O | Cl | Cl |
| 1.169 | C₂H₅ | H | H | 0 | CH₃ | H | CH₃ | H | S | Cl | Cl |
| 1.170 | C₂H₅ | H | H | 2 | CH₃ | H | CH₃ | H | S | Cl | Cl |
| 1.171 | C₂H₅ | H | H | 0 | CH₃ | H | CH₃ | H | SO₂ | Cl | Cl |
| 1.172 | C₂H₅ | H | H | 2 | CH₃ | H | CH₃ | H | SO₂ | Cl | Cl |
| 1.173 | C₂H₅ | H | H | 0 | CH₃ | CH₃ | H | H | O | Cl | Cl |
| 1.174 | C₂H₅ | H | H | 2 | CH₃ | CH₃ | H | H | O | Cl | Cl |
| 1.175 | C₂H₅ | H | H | 0 | H | H | CH₃ | CH₃ | O | Cl | Cl |
| 1.176 | C₂H₅ | H | H | 2 | H | H | CH₃ | CH₃ | O | Cl | Cl |

TABLE 1-continued

Compound of the structure

| No. | R⁵ | R⁶ | R⁷ | n | R¹ | R² | R³ | R⁴ | X | L | M |
|---|---|---|---|---|---|---|---|---|---|---|---|
| 1.177 | CH₃ | H | H | 0 | H | H | H | H | O | CH₃ | CH₃ |
| 1.178 | CH₃ | H | H | 2 | H | H | H | H | O | CH₃ | CH₃ |
| 1.179 | CH₃ | H | H | 0 | H | H | H | H | S | CH₃ | CH₃ |
| 1.180 | CH₃ | H | H | 2 | H | H | H | H | S | CH₃ | CH₃ |
| 1.181 | CH₃ | H | H | 0 | H | H | H | H | SO₂ | CH₃ | CH₃ |
| 1.182 | CH₃ | H | H | 2 | H | H | H | H | SO₂ | CH₃ | CH₃ |
| 1.183 | CH₃ | H | H | 0 | CH₃ | H | H | H | O | CH₃ | CH₃ |
| 1.184 | CH₃ | H | H | 2 | CH₃ | H | H | H | O | CH₃ | CH₃ |
| 1.185 | CH₃ | H | H | 0 | CH₃ | H | H | H | S | CH₃ | CH₃ |
| 1.186 | CH₃ | H | H | 2 | CH₃ | H | H | H | S | CH₃ | CH₃ |
| 1.187 | CH₃ | H | H | 0 | CH₃ | H | H | H | SO₂ | CH₃ | CH₃ |
| 1.188 | CH₃ | H | H | 2 | CH₃ | H | H | H | SO₂ | CH₃ | CH₃ |
| 1.189 | CH₃ | H | H | 0 | CH₃ | H | CH₃ | H | O | CH₃ | CH₃ |
| 1.190 | CH₃ | H | H | 2 | CH₃ | H | CH₃ | H | O | CH₃ | CH₃ |
| 1.191 | CH₃ | H | H | 0 | CH₃ | H | CH₃ | H | S | CH₃ | CH₃ |
| 1.192 | CH₃ | H | H | 2 | CH₃ | H | CH₃ | H | S | CH₃ | CH₃ |
| 1.193 | CH₃ | H | H | 0 | CH₃ | H | CH₃ | H | SO₂ | CH₃ | CH₃ |
| 1.194 | CH₃ | H | H | 2 | CH₃ | H | CH₃ | H | SO₂ | CH₃ | CH₃ |
| 1.195 | CH₃ | H | H | 0 | CH₃ | CH₃ | H | H | O | CH₃ | CH₃ |
| 1.196 | CH₃ | H | H | 2 | CH₃ | CH₃ | H | H | O | CH₃ | CH₃ |
| 1.197 | CH₃ | H | H | 0 | H | H | CH₃ | CH₃ | O | CH₃ | CH₃ |
| 1.198 | CH₃ | H | H | 2 | H | H | CH₃ | CH₃ | O | CH₃ | CH₃ |
| 1.199 | C₂H₅ | H | H | 0 | H | H | H | H | O | CH₃ | CH₃ |
| 1.200 | C₂H₅ | H | H | 2 | H | H | H | H | O | CH₃ | CH₃ |
| 1.201 | C₂H₅ | H | H | 0 | H | H | H | H | S | CH₃ | CH₃ |
| 1.202 | C₂H₅ | H | H | 2 | H | H | H | H | S | CH₃ | CH₃ |
| 1.203 | C₂H₅ | H | H | 0 | H | H | H | H | SO₂ | CH₃ | CH₃ |
| 1.204 | C₂H₅ | H | H | 2 | H | H | H | H | SO₂ | CH₃ | CH₃ |
| 1.205 | C₂H₅ | H | H | 0 | CH₃ | H | H | H | O | CH₃ | CH₃ |
| 1.206 | C₂H₅ | H | H | 2 | CH₃ | H | H | H | O | CH₃ | CH₃ |
| 1.207 | C₂H₅ | H | H | 0 | CH₃ | H | H | H | S | CH₃ | CH₃ |
| 1.208 | C₂H₅ | H | H | 2 | CH₃ | H | H | H | S | CH₃ | CH₃ |
| 1.209 | C₂H₅ | H | H | 0 | CH₃ | H | H | H | SO₂ | CH₃ | CH₃ |
| 1.210 | C₂H₅ | H | H | 2 | CH₃ | H | H | H | SO₂ | CH₃ | CH₃ |
| 1.211 | C₂H₅ | H | H | 0 | CH₃ | H | CH₃ | H | O | CH₃ | CH₃ |
| 1.212 | C₂H₅ | H | H | 2 | CH₃ | H | CH₃ | H | O | CH₃ | CH₃ |
| 1.213 | C₂H₅ | H | H | 0 | CH₃ | H | CH₃ | H | S | CH₃ | CH₃ |
| 1.214 | C₂H₅ | H | H | 2 | CH₃ | H | CH₃ | H | S | CH₃ | CH₃ |
| 1.215 | C₂H₅ | H | H | 0 | CH₃ | H | CH₃ | H | SO₂ | CH₃ | CH₃ |
| 1.216 | C₂H₅ | H | H | 2 | CH₃ | H | CH₃ | H | SO₂ | CH₃ | CH₃ |
| 1.217 | C₂H₅ | H | H | 0 | CH₃ | CH₃ | H | H | O | CH₃ | CH₃ |
| 1.218 | C₂H₅ | H | H | 2 | CH₃ | CH₃ | H | H | O | CH₃ | CH₃ |
| 1.219 | C₂H₅ | H | H | 0 | H | H | CH₃ | CH₃ | O | CH₃ | CH₃ |
| 1.220 | C₂H₅ | H | H | 2 | H | H | CH₃ | CH₃ | O | CH₃ | CH₃ |
| 1.221 | CH₃ | H | p-CH₃—C₆H₄—SO₂— | 0 | H | H | H | H | O | H | CH₃ |
| 1.222 | CH₃ | H | p-CH₃—C₆H₄—SO₂— | 2 | H | H | H | H | O | H | CH₃ |
| 1.223 | CH₃ | H | p-CH₃—C₆H₄—SO₂— | 0 | H | H | H | H | S | H | CH₃ |
| 1.224 | CH₃ | H | p-CH₃—C₆H₄—SO₂— | 2 | H | H | H | H | S | H | CH₃ |
| 1.225 | CH₃ | H | p-CH₃—C₆H₄—SO₂— | 0 | H | H | H | H | SO₂ | H | CH₃ |
| 1.226 | CH₃ | H | p-CH₃—C₆H₄—SO₂— | 2 | H | H | H | H | SO₂ | H | CH₃ |
| 1.227 | CH₃ | H | p-CH₃—C₆H₄—SO₂— | 0 | CH₃ | H | H | H | O | H | CH₃ |
| 1.228 | CH₃ | H | p-CH₃—C₆H₄—SO₂— | 2 | CH₃ | H | H | H | O | H | CH₃ |
| 1.229 | CH₃ | H | p-CH₃—C₆H₄-SO₂ | 0 | CH₃ | H | H | H | S | H | CH₃ |
| 1.230 | CH₃ | H | p-CH₃—C₆H₄—SO₂— | 2 | CH₃ | H | H | H | S | H | CH₃ |

TABLE 1-continued

Compound of the structure

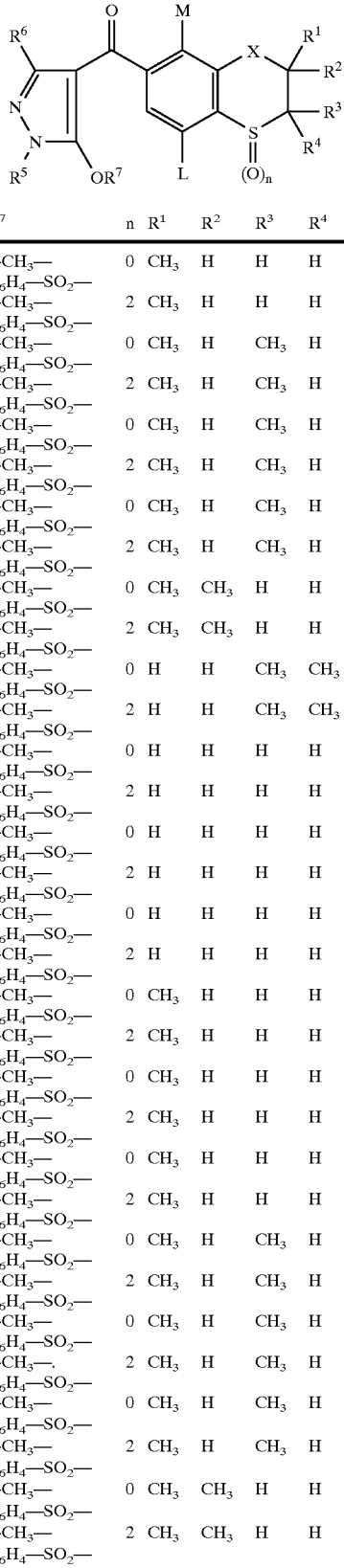

| No. | $R^5$ | $R^6$ | $R^7$ | n | $R^1$ | $R^2$ | $R^3$ | $R^4$ | X | L | M |
|---|---|---|---|---|---|---|---|---|---|---|---|
| 1.231 | $CH_3$ | H | p-$CH_3$—$C_6H_4$—$SO_2$— | 0 | $CH_3$ | H | H | H | $SO_2$ | H | $CH_3$ |
| 1.232 | $CH_3$ | H | p-$CH_3$—$C_6H_4$—$SO_2$— | 2 | $CH_3$ | H | H | H | $SO_2$ | H | $CH_3$ |
| 1.233 | $CH_3$ | H | p-$CH_3$—$C_6H_4$—$SO_2$— | 0 | $CH_3$ | H | $CH_3$ | H | O | H | $CH_3$ |
| 1.234 | $CH_3$ | H | p-$CH_3$—$C_6H_4$—$SO_2$— | 2 | $CH_3$ | H | $CH_3$ | H | O | H | $CH_3$ |
| 1.235 | $CH_3$ | H | p-$CH_3$—$C_6H_4$—$SO_2$— | 0 | $CH_3$ | H | $CH_3$ | H | S | H | $CH_3$ |
| 1.236 | $CH_3$ | H | p-$CH_3$—$C_6H_4$—$SO_2$— | 2 | $CH_3$ | H | $CH_3$ | H | S | H | $CH_3$ |
| 1.237 | $CH_3$ | H | p-$CH_3$—$C_6H_4$—$SO_2$— | 0 | $CH_3$ | H | $CH_3$ | H | $SO_2$ | H | $CH_3$ |
| 1.238 | $CH_3$ | H | p-$CH_3$—$C_6H_4$—$SO_2$— | 2 | $CH_3$ | H | $CH_3$ | H | $SO_2$ | H | $CH_3$ |
| 1.239 | $CH_3$ | H | p-$CH_3$—$C_6H_4$—$SO_2$— | 0 | $CH_3$ | $CH_3$ | H | H | O | H | $CH_3$ |
| 1.240 | $CH_3$ | H | p-$CH_3$—$C_6H_4$—$SO_2$— | 2 | $CH_3$ | $CH_3$ | H | H | O | H | $CH_3$ |
| 1.241 | $CH_3$ | H | p-$CH_3$—$C_6H_4$—$SO_2$— | 0 | H | H | $CH_3$ | $CH_3$ | O | H | $CH_3$ |
| 1.242 | $CH_3$ | H | p-$CH_3$—$C_6H_4$—$SO_2$— | 2 | H | H | $CH_3$ | $CH_3$ | O | H | $CH_3$ |
| 1.243 | $C_2H_5$ | H | p-$CH_3$—$C_6H_4$—$SO_2$— | 0 | H | H | H | H | O | H | $CH_3$ |
| 1.244 | $C_2H_5$ | H | p-$CH_3$—$C_6H_4$—$SO_2$— | 2 | H | H | H | H | O | H | $CH_3$ |
| 1.245 | $C_2H_5$ | H | p-$CH_3$—$C_6H_4$—$SO_2$— | 0 | H | H | H | H | S | H | $CH_3$ |
| 1.246 | $C_2H_5$ | H | p-$CH_3$—$C_6H_4$—$SO_2$— | 2 | H | H | H | H | S | H | $CH_3$ |
| 1.247 | $C_2H_5$ | H | p-$CH_3$—$C_6H_4$—$SO_2$— | 0 | H | H | H | H | $SO_2$ | H | $CH_3$ |
| 1.248 | $C_2H_5$ | H | p-$CH_3$—$C_6H_4$—$SO_2$— | 2 | H | H | H | H | $SO_2$ | H | $CH_3$ |
| 1.249 | $C_2H_5$ | H | p-$CH_3$—$C_6H_4$—$SO_2$— | 0 | $CH_3$ | H | H | H | O | H | $CH_3$ |
| 1.250 | $C_2H_5$ | H | p-$CH_3$—$C_6H_4$—$SO_2$— | 2 | $CH_3$ | H | H | H | O | H | $CH_3$ |
| 1.251 | $C_2H_5$ | H | p-$CH_3$—$C_6H_4$—$SO_2$— | 0 | $CH_3$ | H | H | H | S | H | $CH_3$ |
| 1.252 | $C_2H_5$ | H | p-$CH_3$—$C_6H_4$—$SO_2$— | 2 | $CH_3$ | H | H | H | S | H | $CH_3$ |
| 1.253 | $C_2H_5$ | H | p-$CH_3$—$C_6H_4$—$SO_2$— | 0 | $CH_3$ | H | H | H | $SO_2$ | H | $CH_3$ |
| 1.254 | $C_2H_5$ | H | p-$CH_3$—$C_6H_4$—$SO_2$— | 2 | $CH_3$ | H | H | H | $SO_2$ | H | $CH_3$ |
| 1.255 | $C_2H_5$ | H | p-$CH_3$—$C_6H_4$—$SO_2$— | 0 | $CH_3$ | H | $CH_3$ | H | O | H | $CH_3$ |
| 1.256 | $C_2H_5$ | H | p-$CH_3$—$C_6H_4$—$SO_2$— | 2 | $CH_3$ | H | $CH_3$ | H | O | H | $CH_3$ |
| 1.257 | $C_2H_5$ | H | p-$CH_3$—$C_6H_4$—$SO_2$— | 0 | $CH_3$ | H | $CH_3$ | H | S | H | $CH_3$ |
| 1.258 | $C_2H_5$ | H | p-$CH_3$—$C_6H_4$—$SO_2$— | 2 | $CH_3$ | H | $CH_3$ | H | S | H | $CH_3$ |
| 1.259 | $C_2H_5$ | H | p-$CH_3$—$C_6H_4$—$SO_2$— | 0 | $CH_3$ | H | $CH_3$ | H | $SO_2$ | H | $CH_3$ |
| 1.260 | $C_2H_5$ | H | p-$CH_3$—$C_6H_4$—$SO_2$— | 2 | $CH_3$ | H | $CH_3$ | H | $SO_2$ | H | $CH_3$ |
| 1.261 | $C_2H_5$ | H | p-$CH_3$—$C_6H_4$—$SO_2$— | 0 | $CH_3$ | $CH_3$ | H | H | O | H | $CH_3$ |
| 1.262 | $C_2H_5$ | H | p-$CH_3$—$C_6H_4$—$SO_2$— | 2 | $CH_3$ | $CH_3$ | H | H | O | H | $CH_3$ |

TABLE 1-continued

Compound of the structure

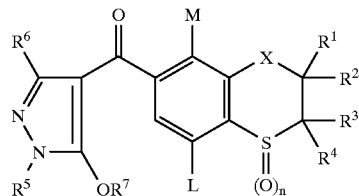

| No. | R⁵ | R⁶ | R⁷ | n | R¹ | R² | R³ | R⁴ | X | L | M |
|---|---|---|---|---|---|---|---|---|---|---|---|
| 1.263 | $C_2H_5$ | H | p-$CH_3$—$C_6H_4$—$SO_2$— | 0 | H | H | $CH_3$ | $CH_3$ | O | H | $CH_3$ |
| 1.264 | $C_2H_5$ | H | p-$CH_3$—$C_6H_4$—$SO_2$— | 2 | H | H | $CH_3$ | $CH_3$ | O | H | $CH_3$ |
| 1.265 | $CH_3$ | $CH_3$ | H | 0 | H | H | H | H | O | H | $CH_3$ |
| 1.266 | $CH_3$ | $CH_3$ | H | 2 | H | H | H | H | O | H | $CH_3$ |
| 1.267 | $CH_3$ | $CH_3$ | H | 0 | H | H | H | H | S | H | $CH_3$ |
| 1.268 | $CH_3$ | $CH_3$ | H | 2 | H | H | H | H | S | H | $CH_3$ |
| 1.269 | $CH_3$ | $CH_3$ | H | 0 | H | H | H | H | $SO_2$ | H | $CH_3$ |
| 1.270 | $CH_3$ | $CH_3$ | H | 2 | H | H | H | H | $SO_2$ | H | $CH_3$ |
| 1.271 | $CH_3$ | $CH_3$ | H | 0 | $CH_3$ | H | H | H | O | H | $CH_3$ |
| 1.272 | $CH_3$ | $CH_3$ | H | 2 | $CH_3$ | H | H | H | O | H | $CH_3$ |
| 1.273 | $CH_3$ | $CH_3$ | H | 0 | $CH_3$ | H | H | H | S | H | $CH_3$ |
| 1.274 | $CH_3$ | $CH_3$ | H | 2 | $CH_3$ | H | H | H | S | H | $CH_3$ |
| 1.275 | $CH_3$ | $CH_3$ | H | 0 | $CH_3$ | H | H | H | $SO_2$ | H | $CH_3$ |
| 1.276 | $CH_3$ | $CH_3$ | H | 2 | $CH_3$ | H | H | H | $SO_2$ | H | $CH_3$ |
| 1.277 | $CH_3$ | $CH_3$ | H | 0 | $CH_3$ | H | $CH_3$ | H | O | H | $CH_3$ |
| 1.278 | $CH_3$ | $CH_3$ | H | 2 | $CH_3$ | H | $CH_3$ | H | O | H | $CH_3$ |
| 1.279 | $CH_3$ | $CH_3$ | H | 0 | $CH_3$ | H | $CH_3$ | H | S | H | $CH_3$ |
| 1.280 | $CH_3$ | $CH_3$ | H | 2 | $CH_3$ | H | $CH_3$ | H | S | H | $CH_3$ |
| 1.281 | $CH_3$ | $CH_3$ | H | 0 | $CH_3$ | H | $CH_3$ | H | $SO_2$ | H | $CH_3$ |
| 1.282 | $CH_3$ | $CH_3$ | H | 2 | $CH_3$ | H | $CH_3$ | H | $SO_2$ | H | $CH_3$ |
| 1.283 | $CH_3$ | $CH_3$ | H | 0 | $CH_3$ | $CH_3$ | H | H | O | H | $CH_3$ |
| 1.284 | $CH_3$ | $CH_3$ | H | 2 | $CH_3$ | $CH_3$ | H | H | O | H | $CH_3$ |
| 1.285 | $CH_3$ | $CH_3$ | H | 0 | H | H | $CH_3$ | $CH_3$ | O | H | $CH_3$ |
| 1.286 | $CH_3$ | $CH_3$ | H | 2 | H | H | $CH_3$ | $CH_3$ | O | H | $CH_3$ |

TABLE 2

Compound [sic] of the structure

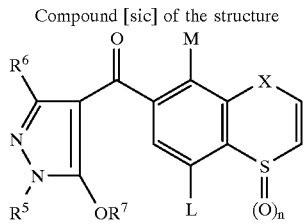

| No. | $R_5$ | $R_6$ | $R_7$ | n | X | L | M |
|---|---|---|---|---|---|---|---|
| 2.1 | $CH_3$ | $CH_3$ | H | 0 | O | H | H |
| 2.2 | $CH_3$ | $CH_3$ | H | 2 | O | H | H |
| 2.3 | $CH_3$ | $CH_3$ | H | 0 | S | H | H |
| 2.4 | $CH_3$ | $CH_3$ | H | 2 | S | H | H |
| 2.5 | $CH_3$ | $CH_3$ | H | 0 | $SO_2$ | H | H |
| 2.6 | $CH_3$ | $CH_3$ | H | 2 | $SO_2$ | H | H |
| 2.7 | $C_2H_5$ | H | H | 0 | O | H | H |
| 2.8 | $C_2H_5$ | H | H | 2 | O | H | H |
| 2.9 | $C_2H_5$ | H | H | 0 | S | H | H |
| 2.10 | $C_2H_5$ | H | H | 2 | S | H | H |
| 2.11 | $C_2H_5$ | H | H | 0 | $SO_2$ | H | H |
| 2.12 | $C_2H_5$ | H | H | 2 | $SO_2$ | H | H |
| 2.13 | $CH_3$ | H | H | 0 | O | H | $CH_3$ |
| 2.14 | $CH_3$ | H | H | 2 | O | H | $CH_3$ |
| 2.15 | $CH_3$ | H | H | 0 | S | H | $CH_3$ |
| 2.16 | $CH_3$ | H | H | 2 | S | H | $CH_3$ |
| 2.17 | $CH_3$ | H | H | 0 | $SO_2$ | H | $CH_3$ |
| 2.18 | $CH_3$ | H | H | 2 | $SO_2$ | H | $CH_3$ |
| 2.19 | $CH_3$ | $CH_3$ | H | 0 | O | H | $CH_3$ |
| 2.20 | $CH_3$ | $CH_3$ | H | 2 | O | H | $CH_3$ |
| 2.21 | $CH_3$ | $CH_3$ | H | 0 | S | H | $CH_3$ |
| 2.22 | $CH_3$ | $CH_3$ | H | 2 | S | H | $CH_3$ |
| 2.23 | $CH_3$ | $CH_3$ | H | 0 | $SO_2$ | H | $CH_3$ |
| 2.24 | $CH_3$ | $CH_3$ | H | 2 | $SO_2$ | H | $CH_3$ |
| 2.25 | $C_2H_5$ | H | H | 0 | O | H | $CH_3$ |
| 2.26 | $C_2H_5$ | H | H | 2 | O | H | $CH_3$ |
| 2.27 | $C_2H_5$ | H | H | 0 | S | H | $CH_3$ |
| 2.28 | $C_2H_5$ | H | H | 2 | S | H | $CH_3$ |
| 2.29 | $C_2H_5$ | H | H | 0 | $SO_2$ | H | $CH_3$ |
| 2.30 | $C_2H_5$ | H | H | 2 | $SO_2$ | H | $CH_3$ |
| 2.31 | $CH_3$ | H | H | 0 | O | H | Cl |
| 2.32 | $CH_3$ | H | H | 2 | O | H | Cl |
| 2.33 | $CH_3$ | H | H | 0 | S | H | Cl |
| 2.34 | $CH_3$ | H | H | 2 | S | H | Cl |
| 2.35 | $CH_3$ | H | H | 0 | $SO_2$ | H | Cl |
| 2.36 | $CH_3$ | H | H | 2 | $SO_2$ | H | Cl |

TABLE 2-continued

Compound [sic] of the structure

| No. | $R_5$ | $R_6$ | $R_7$ | n | X | L | M |
|---|---|---|---|---|---|---|---|
| 2.37 | $CH_3$ | $CH_3$ | H | 0 | O | H | Cl |
| 2.38 | $CH_3$ | $CH_3$ | H | 2 | O | H | Cl |
| 2.39 | $CH_3$ | $CH_3$ | H | 0 | S | H | Cl |
| 2.40 | $CH_3$ | $CH_3$ | H | 2 | S | H | Cl |
| 2.41 | $CH_3$ | $CH_3$ | H | 0 | $SO_2$ | H | Cl |
| 2.42 | $CH_3$ | $CH_3$ | H | 2 | $SO_2$ | H | Cl |
| 2.43 | $C_2H_5$ | H | H | 0 | O | H | Cl |
| 2.44 | $C_2H_5$ | H | H | 2 | O | H | Cl |
| 2.45 | $C_2H_5$ | H | H | 0 | S | H | Cl |
| 2.46 | $C_2H_5$ | H | H | 2 | S | H | Cl |
| 2.47 | $C_2H_5$ | H | H | 0 | $SO_2$ | H | Cl |
| 2.48 | $C_2H_5$ | H | H | 2 | $SO_2$ | H | Cl |
| 2.49 | $CH_3$ | H | H | 0 | O | $CH_3$ | $CH_3$ |
| 2.50 | $CH_3$ | H | H | 2 | O | $CH_3$ | $CH_3$ |
| 2.51 | $CH_3$ | H | H | 0 | S | $CH_3$ | $CH_3$ |
| 2.52 | $CH_3$ | H | H | 2 | S | $CH_3$ | $CH_3$ |
| 2.53 | $CH_3$ | H | H | 0 | $SO_2$ | $CH_3$ | $CH_3$ |
| 2.54 | $CH_3$ | H | H | 2 | $SO_2$ | $CH_3$ | $CH_3$ |
| 2.55 | $CH_3$ | $CH_3$ | H | 0 | O | $CH_3$ | $CH_3$ |
| 2.56 | $CH_3$ | $CH_3$ | H | 2 | O | $CH_3$ | $CH_3$ |
| 2.57 | $CH_3$ | $CH_3$ | H | 0 | S | $CH_3$ | $CH_3$ |
| 2.58 | $CH_3$ | $CH_3$ | H | 2 | S | $CH_3$ | $CH_3$ |
| 2.59 | $CH_3$ | $CH_3$ | H | 0 | $SO_2$ | $CH_3$ | $CH_3$ |
| 2.60 | $CH_3$ | $CH_3$ | H | 2 | $SO_2$ | $CH_3$ | $CH_3$ |
| 2.61 | $C_2H_5$ | H | H | 0 | O | $CH_3$ | $CH_3$ |
| 2.62 | $C_2H_5$ | H | H | 2 | O | $CH_3$ | $CH_3$ |
| 2.63 | $C_2H_5$ | H | H | 0 | S | $CH_3$ | $CH_3$ |
| 2.64 | $C_2H_5$ | H | H | 2 | S | $CH_3$ | $CH_3$ |
| 2.65 | $C_2H_5$ | H | H | 0 | $SO_2$ | $CH_3$ | $CH_3$ |
| 2.66 | $C_2H_5$ | H | H | 2 | $SO_2$ | $CH_3$ | $CH_3$ |
| 2.67 | $CH_3$ | H | p-$CH_3$—$C_6H_4$—$SO_2$— | 0 | O | H | $CH_3$ |
| 2.68 | $CH_3$ | H | p-$CH_3$—$C_6H_4$—$SO_2$— | 2 | O | H | $CH_3$ |
| 2.69 | $CH_3$ | H | p-$CH_3$—$C_6H_4$—$SO_2$— | 0 | S | H | $CH_3$ |
| 2.70 | $CH_3$ | H | p-$CH_3$—$C_6H_4$—$SO_2$— | 2 | S | H | $CH_3$ |
| 2.71 | $CH_3$ | H | p-$CH_3$—$C_6H_4$—$SO_2$— | 0 | $SO_2$ | H | $CH_3$ |
| 2.72 | $CH_3$ | H | p-$CH_3$—$C_6H_4$—$SO_2$— | 2 | $SO_2$ | H | $CH_3$ |
| 2.73 | $CH_3$ | H | p-$CH_3$—$C_6H_4$—$SO_2$— | 0 | O | H | $CH_3$ |
| 2.74 | $C_2H_5$ | H | p-$CH_3$—$C_6H_4$—$SO_2$— | 0 | O | H | $CH_3$ |
| 2.75 | $C_2H_5$ | H | p-$CH_3$—$C_6H_4$—$SO_2$— | 2 | O | H | $CH_3$ |
| 2.76 | $C_2H_5$ | H | p-$CH_3$—$C_6H_4$—$SO_2$— | 0 | S | H | $CH_3$ |
| 2.77 | $C_2H_5$ | H | p-$CH_3$—$C_6H_4$—$SO_2$— | 2 | S | H | $CH_3$ |
| 2.78 | $C_2H_5$ | H | p-$CH_3$—$C_6H_4$—$SO_2$— | 0 | $SO_2$ | H | $CH_3$ |
| 2.79 | $C_2H_5$ | H | p-$CH_3$—$C_6H_4$—$SO_2$— | 2 | $SO_2$ | H | $CH_3$ |

PREPARATION EXAMPLES

A) Preparation examples of the starting materials and intermediates

1. Ethyl 3-(2-bromoethoxy)-2-methylbenzoate 13.6 g (0.2 mol) of sodium methylate are dissolved in 200 ml of ethanol. 36 g (0.2 mol) of ethyl 3-hydroxy-2-methylbenzoate are then added and the mixture refluxed for 2 hours. 61.4 g (0.32 mol) of 1,2-dibromoethane are subsequently added dropwise and the mixture is refluxed for 20 hours. When cold, the reaction mixture is concentrated on a rotary evaporator. The residue is taken up in ethyl acetate and washed 3 times with dilute sodium hydroxide solution. The organic phase is dried and the solvent is distilled off. The product of value is purified by column chromatography.

Yield: 14.6 g of oil

NMR(270 MHZ; $CDCl_3$; δ in ppm): 7.4 (d, 1H), 7.2 (tr, 1H), 6.9 (d, 1H), 4.4 (tr, 2H), 4.3 (q, 2H), 3.7 (tr, 2H), 2.4 (s, 3H), 1.5 (tr, 3H)

2. Ethyl 3-(2-methylsulfonylthioethoxy)-2-methylbenzoate 2 g (7 mmol) of ethyl 3-(2-bromoethoxy)-2-methylbenzoate and 1.1 g (7.3 mmol) of potassium thiomethanesulfonate are dissolved in 10 ml absolute ethanol. The reaction mixture is refluxed for 20 hours. The solvent is then distilled off and the residue taken up in methylene chloride and washed with water. The organic phase is dried over sodium sulfate and the solvent is removed. The product of value is purified by column chromatography.

Yield: 1.1 g (50%)

NMR(270 MHZ; $CDCl_3$; δ in ppm): 7.4 (d, 1H), 7.2 (tr, 1H), 7.0 (d, 1H), 4.5 (tr, 2H), 4.3 (q, 2H), 3.6 (tr, 2H), 3.4 (s, 3H), 2.4 (s, 3H), 1.4 (tr, 3H)

3. Ethyl 8-methyl-2,3-dihydrobenz-1,4-oxathiine-7-carboxylate 1.0 g (3.4 mmol) of ethyl 3-(2-methylsulfonylthioethoxy)-2-methylbenzoate are dissolved in 5 ml of nitromethane. 0.42 g (3.14 mmol) of aluminum trichloride is added. The mixture is stirred for 45 minutes at room temperature. Working-up is carried out by adding 10 ml of 2 N hydrochloric acid and subsequent extraction using MTB ether. The combined organic phases are washed with water and sodium carbonate solution, and dried over sodium sulfate, and the solvent is distilled off.

Yield: 0.7 g (93%)

NMR(270 MHZ; $CDCl_3$; δ in ppm): 7.5 (d, 1H), 6.9 (d, 1H), 4.5 (tr, 2H), 4.3 (q, 2H), 3.2 (tr, 2H), 2.4 (s, 3H), 1.4 (tr, 3H)

4. 8-Methyl-2,3-dihydrobenz-1, 4-oxathiine-7-carboxylic acid 4.0 g (0.0168 mol) of ethyl 8-methyl-2,3-dihydrobenz-1,4-oxathiine-7-carboxylate together with 1.0 g (0.0252 mol) of sodium hydroxide are refluxed in 40 ml of methanol/water. The mixture is stirred for 2 hours at this temperature, and the solvent is subsequently distilled off. The residue is taken up in water. The mixture is extracted using ether, and the aqueous phase is then acidified using 2 N hydrochloric acid. The product of value precipitates and is filtered off with suction and washed with a small amount of water. The product is dried in a vacuum drying oven at 40° C.

Yield: 2.9 g (82%)

NMR(270 MHZ; $d^6$ DMSO; δ in ppm): 12.3 (bs, 1H), 7.3 (d, 1H), 6.9 (d, 1H), 4.4 (tr, 2H), 3.2 (tr, 2H), 2.4 (s, 3H)

5. 8-Methyl-2,3-dihydro-4,4-dioxobenz-1,4-oxathiine-7-carboxylic acid 2.8 g (0.013 mol) of 8-methyl-2,3-dihydrobenz-1,4-oxathiine-7-carboxylic acid together with a spatula-tip full of sodium tungstate are introduced into 30 ml of acetic acid. The mixture is heated to 50° C. 3.3 g (0.029 mol) of hydrogen peroxide (30% strength) are added dropwise. The reaction solution is held at 50–60° C. for a further 4 hours. The solution is poured into ice-water. The precipitate is filtered off with suction, washed with water and dried in a vacuum drying oven at 40° C.

Yield: 2.7 g

Melting point: 234° C.

TABLE 3

Structure III: A carbonyl-substituted benzoxathiine with substituents T (on C=O), M, L on the aromatic ring, X in the ring, R¹, R², R³, R⁴ on the saturated ring carbons, and $(O)_n$ on sulfur.

| No. | T | R¹ | R² | R³ | R⁴ | X | M | L | n | Physical data |
|---|---|---|---|---|---|---|---|---|---|---|
| 3.1 | OC$_2$H$_5$ | H | H | H | H | O | CH$_3$ | H | 0 | 1H-NMR (270 MHz; CDCl$_3$; in ppm): 7.5 (d, 1H), 6.9(d, 1H), 4.5(tr, 2H), 4.3(q, 2H), 3.2(tr, 2H), 2.4 (s, 3H), 1.4 tr, 3H) |
| 3.2 | HO | H | H | H | H | O | CH$_3$ | H | 0 | 1H-NMR (270 MHz; d$^6$-DMSO; in ppm): 12.3(bs, 1H), 7.3(d, 1H), 6.9(d, 1H), 4.4 (tr, 2H), 3.2(tr, 2H), 2.4(s, 3H) |
| 3.3 | HO | H | H | H | H | O | CH$_3$ | H | 2 | m.p. [° C.]: 234 |
| 3.4 | OCH$_3$ | H | H | H | H | S | CH$_3$ | H | 0 | m.p. [° C.]: 57 |
| 3.5 | OH | H | H | H | H | S | CH$_3$ | H | 0 | m.p. [° C.]: 179 |
| 3.6 | OH | H | H | H | H | SO$_2$ | CH$_3$ | H | 2 | 1H-NMR (250 MHz, d$^6$-DMSO): 13.8(bs), 8.11(d), 7.98(d), 4.40(m), 2.80(s) |
| 3.7 | OC$_2$H$_5$ | H | H | H | H | O | Cl | H | 0 | 1H-NMR (CDCl$_3$): 7.3(2x d), 4.4(q), 4.5(tr), 3.2(tr), 1.4 (tr) |
| 3.8 | OH | H | H | H | H | O | Cl | H | 0 | m.p. [° C.]: 209° C. |
| 3.9 | OH | H | H | H | H | O | Cl | H | 2 | m.p. [° C.]: 225 |

TABLE 4

| No. | T | R1 | R4 | X | M | L | n | Physical data |
|---|---|---|---|---|---|---|---|---|
| 4.1 | OC$_2$H$_5$ | H | H | O | CH$_3$ | H | 0 | 1H-NMR (270 MHz, CDCl$_3$): 7.44 (d), 6.85(d), 6.50(d), 5.25 (d), 4.32(q), 2.36(s), 1.36 (tr) |
| 4.2 | OH | H | H | O | CH$_3$ | H | 0 | m.p. [° C.]: 174 |
| 4.3 | OH | H | H | O | CH$_3$ | H | 2 | m.p. [° C.]: 205 |
| 4.4 | OC$_2$H$_5$ | H | H | O | Cl | H | 0 | m.p. [° C.]: 92 |
| 4.5 | OH | H | H | O | Cl | H | 0 | m.p. [° C.]: 201 |

Preparation of the end products 4-(8-Methyl-2,3-dihydro-4,4-dioxobenz[1,4]oxathiin-7-yl-carbonyl)-1-ethyl-5-hydroxypyrazole 0.9 g (3.72 mmol) of 8-methyl-2,3-dihydro-4,4-dioxobenz-1,4-oxathiine-7-carboxylic acid together with 0.42 g (3.72 mmol) of 1-ethylpyrazolone are introduced into 20 ml of acetonitrile. 0.81 g (3.9 mmol) of DCC is then added and the mixture is stirred for several hours at RT. 0.75 g (7.44 mmol) of triethylamine and 0.2 ml of trimethylsilyl cyanide are subsequently added and the mixture is stirred for 3 hours at RT.

Working-up is carried out by adding 100 ml of 2% sodium carbonate solution and removing the precipitate by filtration with suction. The filtrate is washed with ethyl acetate and brought to pH 4 using 2 N HCl, and the product of value is extracted.

The organic phase is dried and concentrated on a rotary evaporator.

The product is purified by recrystallization.

Yield: 0.3 g of solid

Melting point: 184° C.

TABLE 5

| No. | R1 | R2 | R3 | R4 | R5 | R6 | R7 | X | M | L | n | Physical data |
|---|---|---|---|---|---|---|---|---|---|---|---|---|
| 5.1 | H | H | H | H | $C_2H_5$ | H | H | O | $CH_3$ | H | 2 | m.p. [° C]: 184 |
| 5.2 | H | H | H | H | $CH_3$ | H | H | O | $CH_3$ | H | 0 | m.p. [° C]: 112 |
| 5.3 | H | H | H | H | $C_2H_5$ | H | H | $SO_2$ | $CH_3$ | H | 2 | 1H-NMR (270 MHz, $d^6$-DMSO): 7.97 (d), 7.80(d), 7.45(s), 4.41(s), 3.90(q), 2.59(s), 1.26(tr) |
| 5.4 | H | H | H | H | $CH_3$ | H | H | S | $CH_3$ | H | 0 | m.p. [° C]: 114 |
| 5.5 | H | H | H | H | $C_2H_5$ | H | H | S | $CH_3$ | H | 0 | m.p. [° C]: 81 |
| 5.6 | H | H | H | H | $C_2H_5$ | H | H | O | Cl | H | 0 | m.p. [° C]: 114 |

TABLE 6

| No. | R5 | R6 | R7 | R1 | R4 | X | M | L | n | Physical data |
|---|---|---|---|---|---|---|---|---|---|---|
| 6.1 | nPropyl | H | H | H | H | O | $CH_3$ | H | 0 | 1H-NMR (270 MHz, $CDCl_3$): 8.96 (bs), 7.43(s), 7.09(d), 6.81(d), 6.50(d), 5.26(d), 3.98(tr) 2.22(s), 1.89(m), 0.95(tr) |
| 6.2 | $CH_3$ | H | H | H | H | O | $CH_3$ | H | 0 | m.p. [° C.]: 56° C. |

The compounds I and their agriculturally useful salts are suitable as herbicides, both in the form of isomer mixtures and in the form of the pure isomers. The herbicidal compositions comprising I are capable of controlling vegetation on non-crop areas very efficiently, especially at high rates of application. In crops such as wheat, rice, maize, soya and cotton, they act against broad-leaved weeds and grass weeds without causing any significant damage to the crop plants. This effect is observed mainly at low rates of application.

Depending on the application method in question, the compounds I, or compositions comprising them, can additionally be employed in a further number of crop plants for eliminating undesirable plants. Examples of suitable crops are the following:

Allium cepa, Ananas comosus, Arachis hypogaea, Asparagus officinalis, Beta vulgaris spp. altissima, Beta vulgaris spp. [sic] rapa, Brassica napus var. napus, Brassica napus var. napo-brassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago sativa, Musa spp., Nicotiana tabacum (N.rustica), Olea europaea, Oryza sativa, Phaseolus lunatus, Phaseolus vulgaris, Picea abies, Pinus spp., Pisum sativum, Prunus avium, Prunus persica, Pyrus communis, Ribes sylestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera, Zea mays.

In addition, the compounds I can be used in crops which tolerate the action of herbicides due to breeding including genetic engineering methods.

The herbicidal compositions or the active ingredients can be applied pre- or post-emergence. If the active ingredients are less well tolerated by certain crop plants, application techniques may be used in which the herbicidal compositions are sprayed, with the aid of a spraying apparatus, in such a way that they come into as little contact as possible, if any, with the leaves of the sensitive crop plants, while the active ingredients reach the leaves of undesirable plants which grow underneath, or the exposed soil surface (post-directed, lay-by).

The compounds I, or the herbicidal compositions comprising them, can be used for example in the form of directly sprayable aqueous solutions, powders, suspensions, also highly concentrated aqueous, oily or other suspensions or dispersions, emulsions, oil dispersions, pastes, dusts, materials for spreading or granules by means of spraying, atomizing, dusting, spreading or pouring. The use forms depend on the intended purposes; in any case, they should ensure the finest possible distribution of the active ingredients according to the invention.

Suitable inert additives are essentially: mineral oil fractions of medium to high boiling point, such as kerosine or diesel oil, further coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, alcohols, such as methanol, ethanol, propanol, butanol, cyclohexanol, ketones, such as cyclohexanone, or strongly polar solvents, e.g. amines, such as N-methylpyrrolidone, or water.

Aqueous use forms can be prepared from emulsion concentrates, suspensions, pastes, wettable powders or water-dispersible granules by adding water. To prepare emulsions, pastes or oil dispersions, the substrates [sic], as such or dissolved in an oil or solvent, can be homogenized in water by means of wetting agent, tackifier, dispersant or emulsifier. Alternatively, it is possible to prepare concentrates composed of active substance, wetting agent, tackifier, dispersant or emulsion and, if desired, solvent or oil, these concentrates being suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and the salts of sulfated hexa-, hepta- and octadecanols and of fatty alcohol glycol ether, condensates of sulfonated naphthalene and its derivatives with formaldehyde, condensates of naphthalene, or of naphthalenesulfonic acids, with phenol and formaldehyde, polyoxyethylene octylphenol [sic] ether, ethoxylated isooctyl-, octyl- or nonylphenol, alkylphenol polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite liquors or methylcellulose.

Powders, materials for spreading and dusts can be prepared by mixing or concomitantly grinding reactive substances with a solid carrier. Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin, such as cereal meal, tree bark meal, wood meal and nutshell meal, cellulose powders, or other solid carriers.

The concentrations of the active ingredients I in the ready-to-use preparations can be varied within wide ranges. In general, the formulations comprise from 0.001 to 98% by weight, preferably 0.01 to 95% by weight, of active ingredient. The active ingredients are employed in a purity of from 90% to 100%, preferably 95% to 100% (according to NMR spectrum).

The compounds I according to the invention can be formulated for example as follows:

I. 20 parts by weight of the compound No. 5.1 are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of the compound No. 5.1 are dissolved in a mixture composed of 40 parts by weight of cyclohexanone, 30 parts by weight of isobutanol, 20 parts by weight of the adduct of 40 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. 5.1 are dissolved in a mixture composed of 25 parts by weight of cyclohexanone, 65 parts by weight of a mineral oil fraction of boiling boiling 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. 5.1 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel and the mixture is ground in a hammer mill. Finely distributing the mixture into 20,000 parts by weight of water gives a spray mixture which comprises 0.1% by weight of the active ingredient.

V. 3 parts by weight of the active ingredient No. 5.1 are mixed with 97 parts by weight of finely divided kaolin. This gives a dust which comprises 3% by weight of the active ingredient.

VI. 20 parts by weight of the active ingredient No. 5.1 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound 5.1 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound 5.1 is dissolved in a mixture composed of 80 parts by weight of cyclohexanone and 20 parts by weight of Emulphor EL (ethoxylated castor oil). This gives a stable emulsion concentrate.

To widen the spectrum of action and to achieve synergistic effects, the pyrazol-4-yl-hetaroyl derivatives I can be mixed with a large number of representatives of other groups of herbicidal or growth-regulating active ingredients and applied jointly. Suitable components for mixtures are, for example, 1,2,4-thiadiazoles, 1,3,4-thiadiazoles, amides, aminophosphoric acid and its derivatives, aminotriazoles, anilides, (het)aryloxy-alkanoic acid [sic] and their derivatives, benzoic acid and its derivatives, benzothiadiazinones, 2-aroyl-1,3-cyclohexanediones, hetaryl aryl ketones, benzylisoxazolidinones, meta-CF3-phenyl [sic] derivatives, carbamates, quinolinecarboxylic acid and its derivatives, chloro acetanilide, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- or hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfon-amides, sulfonylureas, triazines, triazinones, triazolinones, triazolecarboxamides and uracils.

It may furthermore be advantageous to apply the compounds I, alone or in combination with other herbicides, even in a mixture with still further crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates may also be added.

Depending on the intended purpose, the season, the target plants and the growth stage, the rates of application of active ingredient are from 0.001 to 3.0, preferably 0.01 to 1.0, kg of active substance (a.s.) per ha.

USE EXAMPLES

The herbicidal activity of the pyrazol-4-yl-hetaroyl derivatives of the formula I was demonstrated by greenhouse experiments:

The culture containers used were plastic flowerpots containing loamy sand with approximately 3.0% of humus as the substrate. The seeds of the test plants were sown separately for each species.

In the case of pre-emergence treatment, the active ingredients, which were suspended or emulsified in water, were applied directly after sowing by means of finely distributing nozzles. The containers were irrigated gently to promote germination and growth and subsequently covered with translucent plastic hoods until the plants had rooted. This cover causes uniform germination of the test plants unless this was adversely affected by the active ingredients.

For the post-emergence treatment, the test plants were first grown to a plant height of from 3 to 15 cm, depending on the plant habit, and only then treated with the active ingredient which had been suspended or emulsified in water. For this purpose, the test plants are either sown directly and grown in the same containers, or they are first grown separately as seedlings and transplanted into the test containers a few days prior to treatment. The rate of application for the pre-emergence treatment was 0.0625 or 0.0313 kg of a.s./ha.

Depending on the species, the plants were kept at from 10–25° C. or 20–35° C. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage or normal course of growth.

The plants used in the greenhouse experiments belong to the following species:

| Scientific name | Common name |
| --- | --- |
| *Chenopodium album* (CHEAL) | lambsquarters (goosefoot) |
| *Echinochloa crus-galli* (ECHCG) | barnyardgrass |
| *Solanum nigrum* (SOLNI) | black nightshade |
| *Triticum aestivum* (TRZAW) | winter wheat |
| *Zea mays* (ZEAMX) | Indian corn |

TABLE 7

Selective herbicidal activity on post-emergence application in the greenhouse

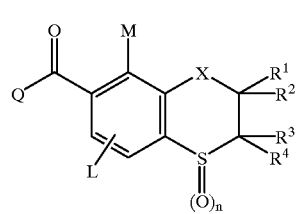

| Rate of application (kg of a.s./ha) Test plants | 0,0625 | 0,0313 |
| --- | --- | --- |
| | Damage in % | |
| ZEAMX | 10 | 10 |
| ECHCG | 90 | 90 |
| CHEAL | 100 | 100 |
| POLPE | 85 | 85 |
| SOLNI | 85 | 85 |

We claim:
1. A pyrazol-4-yl-hetaroyl derivative of the formula I where the substituents have the following meanings:
L and M are hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen, cyano, nitro;

X is oxygen or sulfur which can be substituted by one or two oxygens;

n is zero, one, two;

$R^1$ is hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen;
phenyl which may be mono- or polysubstituted by the following groups: $C_1$–$C_4$-alkyl, hydrogen, $C_1$–$C_4$- alkoxy, $C_1$–$C_4$-haloalkyl, $C_1$–$C_4$-haloalkoxy, halogen, nitro, cyano, $C_1$–$C_4$-alkyloxycarbonyl;

$R^2$ is hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen;

phenyl which may be mono- or polysubstituted by the following groups: $C_1$–$C_4$-alkyl, hydrogen, $C_1$–$C_4$-alkoxy, $C_1$–$C_4$-haloalkyl, $C_1$–$C_4$-haloalkoxy, halogen, nitro, cyano, $C_1$–$C_4$-alkyloxycarbonyl; $R^2$ and $R^3$ may form a linkage;

$R^3$ is hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; substituted phenyl; halogen; $R^3$ and $R^2$ may form a linkage;

phenyl which may be mono- or polysubstituted by the following groups: $C_1$–$C_4$-alkyl, hydrogen, $C_1$–$C_4$-alkoxy, $C_1$–$C_4$-haloalkyl, $C_1$–$C_4$-haloalkoxy, halogen, nitro, cyano, $C_1$–$C_4$-alkyloxycarbonyl; $R^3$ and $R^2$ may form a linkage;

$R^4$ is hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen;

phenyl which may be mono- or polysubstituted by the following groups: $C_1$–$C_4$-alkyl, hydrogen, $C_1$–$C_4$-alkoxy, Cl-$C_4$-haloalkyl, $C_1$–$C_4$-haloalkoxy, halogen, nitro, cyano, $C_1$–$C_4$-alkyloxycarbonyl;

Q is a pyrazole ring, linked in the 4-position, of the formula II

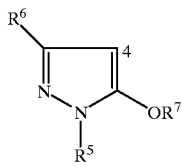

where
$R^5$ is $C_1$–$C_4$-alkyl,
$R^6$ is hydrogen, $C_1$–$C_4$-alkyl or $C_1$–$C_4$-haloalkyl and
$R^7$ is hydrogen, $C_1$–$C_4$-alkylsulfonyl, phenylsulfonyl or alkylphenylsulfonyl, or an agriculturally useful salt thereof.

2. A pyrazol-4-yl-hetaroyl derivative of the formula Ia

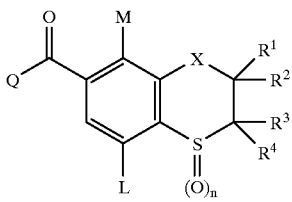

where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and Q, X, $R_1$ to $R_4$ and n have the meanings given in claim 1.

3. A pyrazol-4-yl-hetaroyl derivative of the formula Ib

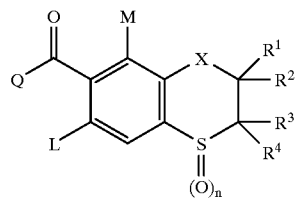

where L is $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and Q, X, $R_1$ to $R_4$ and n have the meanings given in claim 1.

4. A pyrazol-4-yl-hetaroyl derivative of the formula I as claimed in claim 1 where the radicals L and M are hydrogen, methyl, methoxy, chlorine, cyano, nitro and trifluoromethyl.

5. A pyrazol-4-yl-hetaroyl derivative of the formula Ic

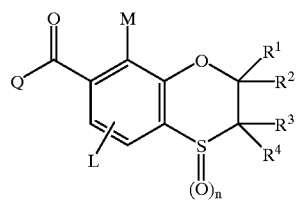

where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and Q, $R_1$ to $R_4$ and n have the meanings given in claim 1.

6. A pyrazol-4-yl-hetaroyl derivative of the formula Id

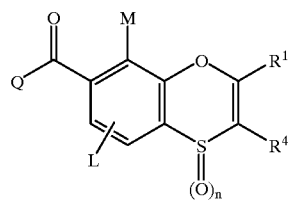

where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and Q, $R_1$, $R_4$ and n have the meanings given in claim 1.

7. A pyrazol-4-yl-hetaroyl derivative of the formula Id

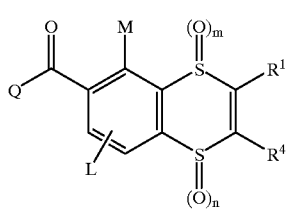

where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and m is zero, one or two and Q, $R_1$, $R_4$ and n have the meanings given in claim 1.

8. A pyrazol-4-yl-hetaroyl derivative of the formula Ie

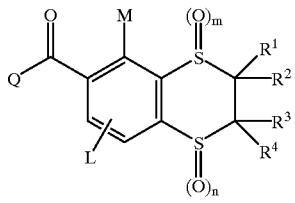

where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, cyano or nitro and m is zero, one or two and Q, $R_1$ to $R_4$ and n have the meanings given in claim 1.

9. A process for the preparation of a compound of the formula I as claimed in claim 1, which comprises acylating the respective starting materials of the formula IIa

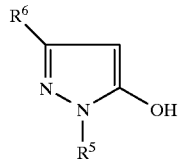

with an acid chloride of the formula IIIa or an acid of the formula IIIb

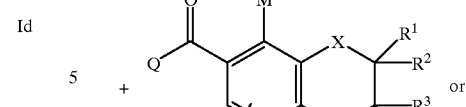

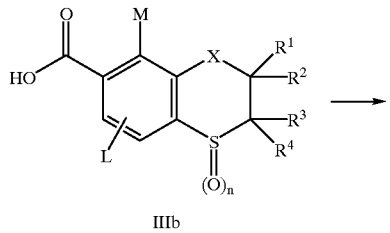

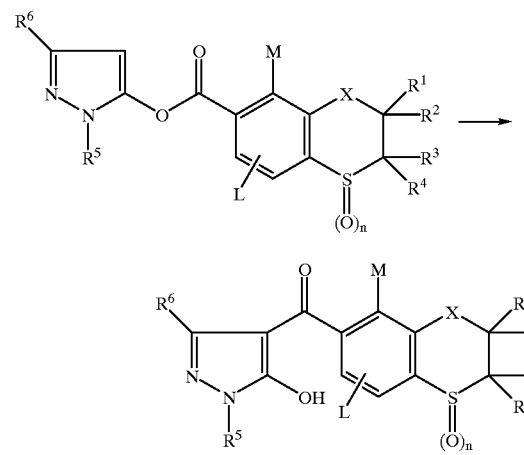

where L, M, X, $R^1$ to $R^4$, $R^5$, $R^6$ and n have the meanings given in claim 1 and subjecting the acylation product to a rearrangement reaction in the presence of a catalyst to give the compound I.

10. A herbicidal composition, comprising at least one pyrazol-4-yl-hetaroyl derivative of the formula I as claimed in claim 1 and customary inert additives.

11. A method for controlling undesirable vegetation, which comprises allowing a herbicidally active amount of a pyrazol-4-yl-hetaroyl derivative of the formula I as claimed in claim 1 to act on the plants or their environment.

* * * * *